(12) United States Patent
Cosgrove et al.

(10) Patent No.: US 9,734,303 B2
(45) Date of Patent: Aug. 15, 2017

(54) CONTROLLED INVENTORY REFRIGERATED DISPENSING SYSTEM

(71) Applicant: Minibar Systems, Rockville, MD (US)

(72) Inventors: Mark T. Cosgrove, Edgewater, MD (US); Paul Knox, Llandeilo (GB)

(73) Assignee: MINIBAR AG (CH)

( * ) Notice: Subject to any disclaimer, the term of this patent is extended or adjusted under 35 U.S.C. 154(b) by 389 days.

(21) Appl. No.: 14/259,621

(22) Filed: Apr. 23, 2014

(65) Prior Publication Data

US 2014/0316799 A1    Oct. 23, 2014

Related U.S. Application Data

(60) Provisional application No. 61/815,045, filed on Apr. 23, 2013.

(51) Int. Cl.
*G06Q 10/00* (2012.01)
*G06Q 50/00* (2012.01)
(Continued)

(52) U.S. Cl.
CPC .......... *G06F 19/3462* (2013.01); *G07F 9/105* (2013.01); *G07F 11/002* (2013.01);
(Continued)

(58) Field of Classification Search
CPC .......... G07F 7/06; G07F 11/002; G07F 13/10; G07F 9/006; G07F 13/02; G07F 9/026;
(Continued)

(56) References Cited

U.S. PATENT DOCUMENTS 4,190,179 A * 2/1980 Moss ............... G07F 11/30
                                           221/299
4,629,090 A    12/1986 Harris et al.
(Continued)

FOREIGN PATENT DOCUMENTS

WO    2011/049167    4/2011
WO    2014031976    2/2014

OTHER PUBLICATIONS

International Search Report issued in corresponding International Patent Application No. PCT/US2014/035136 on Sep. 2, 2014.
(Continued)

*Primary Examiner* — Michelle L Le
(74) *Attorney, Agent, or Firm* — Whiteford, Taylor & Preston, LLP; Gregory M. Stone

(57) ABSTRACT

A vending refrigerator for dispensing pharmaceutical products, such as vials, bottles, syringes, and the like, at a point of distribution, e.g., a doctor's office or pharmacy. The vending refrigerator comprises a first product dispenser for one type of packaging and a second product dispenser for a second type of packaging. The product can be removed from a dispenser drawer but cannot be placed back into the dispenser through the drawer. The product dispensers are filled through openings that are not accessible during normal operations, but that are accessible during refilling procedures. The refrigerator may include a shelf where products that are mistakenly pulled from the product dispenser or that contain multiple doses of their contents can be placed for temporary storage. In some embodiments, the refrigerator comprises a chilled compartment and a freezer compartment.

23 Claims, 22 Drawing Sheets

(51) Int. Cl.
*G06F 19/00* (2011.01)
*G07F 11/00* (2006.01)
*G07F 9/10* (2006.01)
*G07F 11/18* (2006.01)
*G07F 17/00* (2006.01)
*G06Q 10/08* (2012.01)
*G06Q 50/22* (2012.01)
*G06Q 30/04* (2012.01)

(52) U.S. Cl.
CPC .......... *G07F 11/18* (2013.01); *G07F 17/0092* (2013.01); *G06F 19/328* (2013.01); *G06Q 10/087* (2013.01); *G06Q 30/04* (2013.01); *G06Q 50/22* (2013.01)

(58) Field of Classification Search
CPC .... G07F 13/025; G07F 17/3237; G07F 11/00; G07F 11/62; G07F 17/329; G07F 17/42; G07F 7/088; G07F 9/023; G07F 9/10; G07F 11/10; G07F 11/24; G07F 11/38; G07F 11/52; G07F 11/64; G07F 11/70; G07F 11/72; G07F 13/06; G07F 17/0035; G07F 17/0042; G07F 17/0071; G07F 17/0092; G07F 17/32; G07F 17/3206; G07F 17/3209; G07F 17/3211; G07F 17/3218; G07F 17/322; G07F 17/3223; G07F 17/3225; G07F 17/3239; G07F 17/3244; G07F 17/3246; G07F 17/3248; G07F 17/3253; G07F 17/3262; G07F 17/3272; G07F 17/3288; G07F 19/20; G07F 19/201; G07F 19/2055; G07F 7/0886; G07F 7/1008; G07F 7/1016; G07F 9/00; G07F 9/02; A47F 2003/066; A47F 3/08

USPC .......................................................... 705/2
See application file for complete search history.

(56) References Cited

U.S. PATENT DOCUMENTS

| | | | |
|---|---|---|---|
| 6,019,249 A | 2/2000 | Michael et al. | |
| 6,219,587 B1 | 4/2001 | Ahlin et al. | |
| 6,588,548 B1 * | 7/2003 | Dewitt | G06F 19/3462 186/2 |
| 6,684,126 B2 * | 1/2004 | Omura | G07F 11/04 221/2 |
| 6,788,997 B1 | 9/2004 | Frederick | |
| 6,915,657 B1 | 7/2005 | Wood | |
| 7,686,184 B2 | 3/2010 | Yuyama et al. | |
| 2002/0183882 A1 | 12/2002 | Dearing et al. | |
| 2003/0216831 A1 | 11/2003 | Hart et al. | |
| 2004/0099683 A1 * | 5/2004 | Shows | G06F 19/3462 221/263 |
| 2008/0184719 A1 * | 8/2008 | Lowenstein | F25D 29/00 62/127 |
| 2008/0264962 A1 * | 10/2008 | Schifman | G07F 11/62 221/1 |
| 2009/0187274 A1 * | 7/2009 | Higham | G07C 9/00912 700/237 |
| 2010/0042437 A1 | 2/2010 | Levy et al. | |
| 2011/0108564 A1 * | 5/2011 | Roncari | G07F 11/16 221/1 |
| 2011/0172815 A1 * | 7/2011 | Kim | G07F 17/0092 700/235 |
| 2012/0232693 A1 | 9/2012 | Allinson | |

OTHER PUBLICATIONS

Supplementary European Search Report issued in co-pending European Application No. 14788008.2 on Nov. 30, 2016.

\* cited by examiner

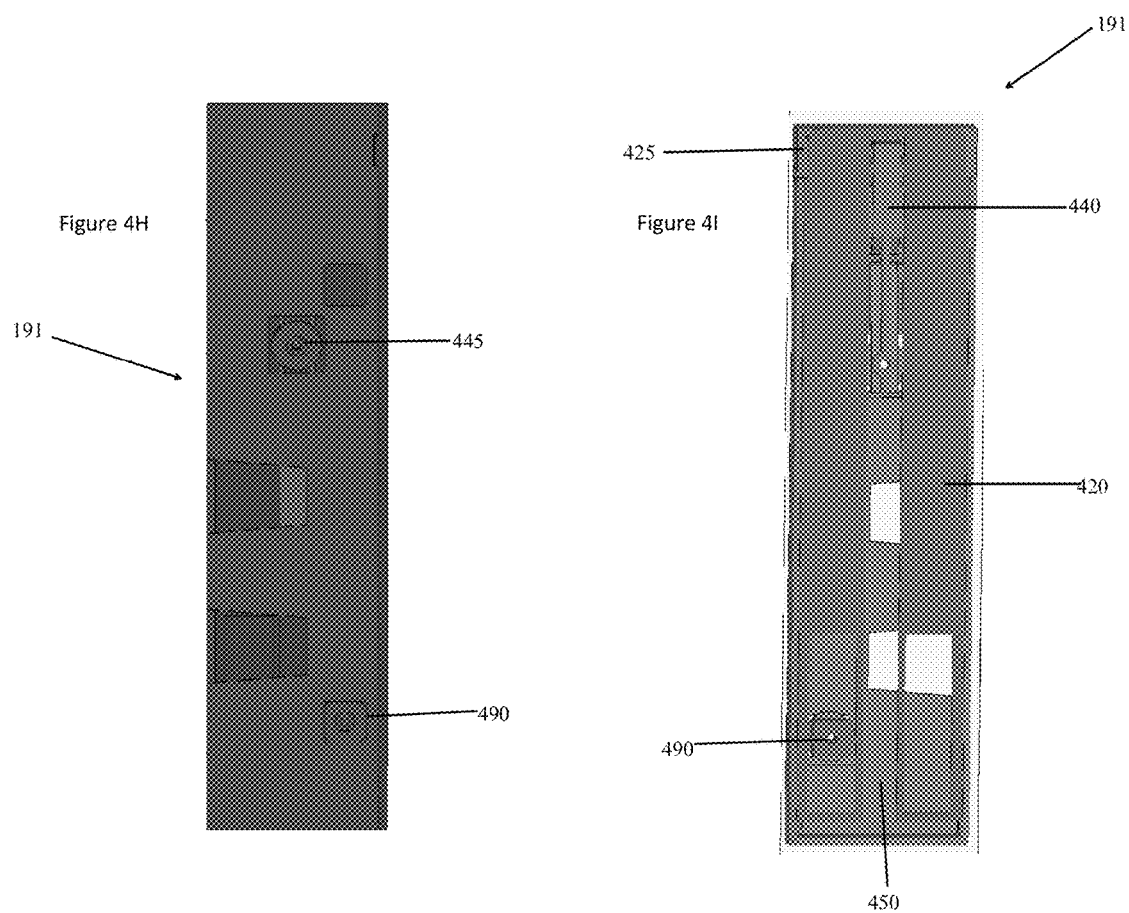

CONTROLLED INVENTORY REFRIGERATED DISPENSING SYSTEM

CROSS-REFERENCE TO RELATED APPLICATIONS

This application claims priority under 35 U.S.C. §119(e) of U.S. Provisional Application Ser. No. 61/815,045, entitled "CONTROLLED INVENTORY REFRIGERATED DISPENSING SYSTEM" filed on Apr. 23, 2013, the specification of which is incorporated herein by reference in its entirety.

BACKGROUND OF THE INVENTION

Field of the Invention

This invention relates generally to refrigerated product storage and dispensing, and more particularly to a refrigeration system for storing products (such as pharmaceutical products) and dispensing such products in a controlled manner that allows automatic tracking of inventory dispensed by and maintained within the refrigerated dispensing unit.

Background

Pharmaceutical products are distributed in many different ways. In many instances, the pharmaceutical product must be kept at a specific temperature in order to ensure its active ingredients retain their chemical properties. For example, some vaccines and antibiotics must be kept refrigerated to ensure that they maintain their pharmaceutical capabilities. In dispensaries, whether pharmacies or doctor's offices, these drug products are typically kept in traditional refrigerators. There is a minimum level of security and maintaining an inventory of the products can be a tedious and labor intensive endeavor.

Existing refrigerators and other such containers do not provide a doctor or pharmacist with an easy and secure method for dispensing medicines that require refrigeration. Thus, there is a need for a refrigerated container that allows physicians, pharmacists, and other individuals responsible for dispensing medicine to easily dispense the products and maintain an accurate inventory of the products.

SUMMARY OF THE INVENTION

The present invention addresses the problems described above and other issues associated with traditional storage of refrigerated products that require a controlled inventory. In one embodiment, a vending refrigerator is provided that comprises a control compartment, comprising a processor configured to manage the vending refrigerator; a first dispensing shelf, communicatively connected with said control compartment; a first product dispenser on the first dispensing shelf and communicatively connected with the first dispensing shelf or control compartment, comprising a storage compartment for a first product and a first dispensing drawer to dispense the first product, wherein the first product cannot be placed back in the first product dispenser through the dispensing drawer; a second dispensing shelf communicatively connected with the control compartment; a second product dispenser on the second dispensing shelf and communicatively connected with the dispensing shelf or control compartment, comprising storage compartment for a second product and a second dispensing drawer to dispense the second product, wherein the second product cannot be placed back in the second product dispenser through the dispensing drawer; and a third dispensing shelf, wherein the third dispensing shelf is capable of storing said first product or second product after said first or second product is dispensed from the first product dispenser or second product dispenser.

BRIEF DESCRIPTION OF THE DRAWINGS

The present invention and various aspects, features, and advantages provided by it are described in detail below with reference to exemplary and non-limiting embodiments and with reference to the drawings, which constitute part of this specification and provide graphic depictions of certain exemplary embodiments. The following is a brief description of the drawings:

FIG. 3I is a left side cross-section of a first product dispenser.

FIG. 4H is a bottom view of the box dispenser.

FIG. 4I is top cross-sectional view of the second product dispenser showing the tray and sensing lever mechanism.

DETAILED DESCRIPTION

The invention summarized above may be better understood by referring to the following description, which should be read in conjunction with the accompanying claims and drawings in which like reference numbers are used for like parts. The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
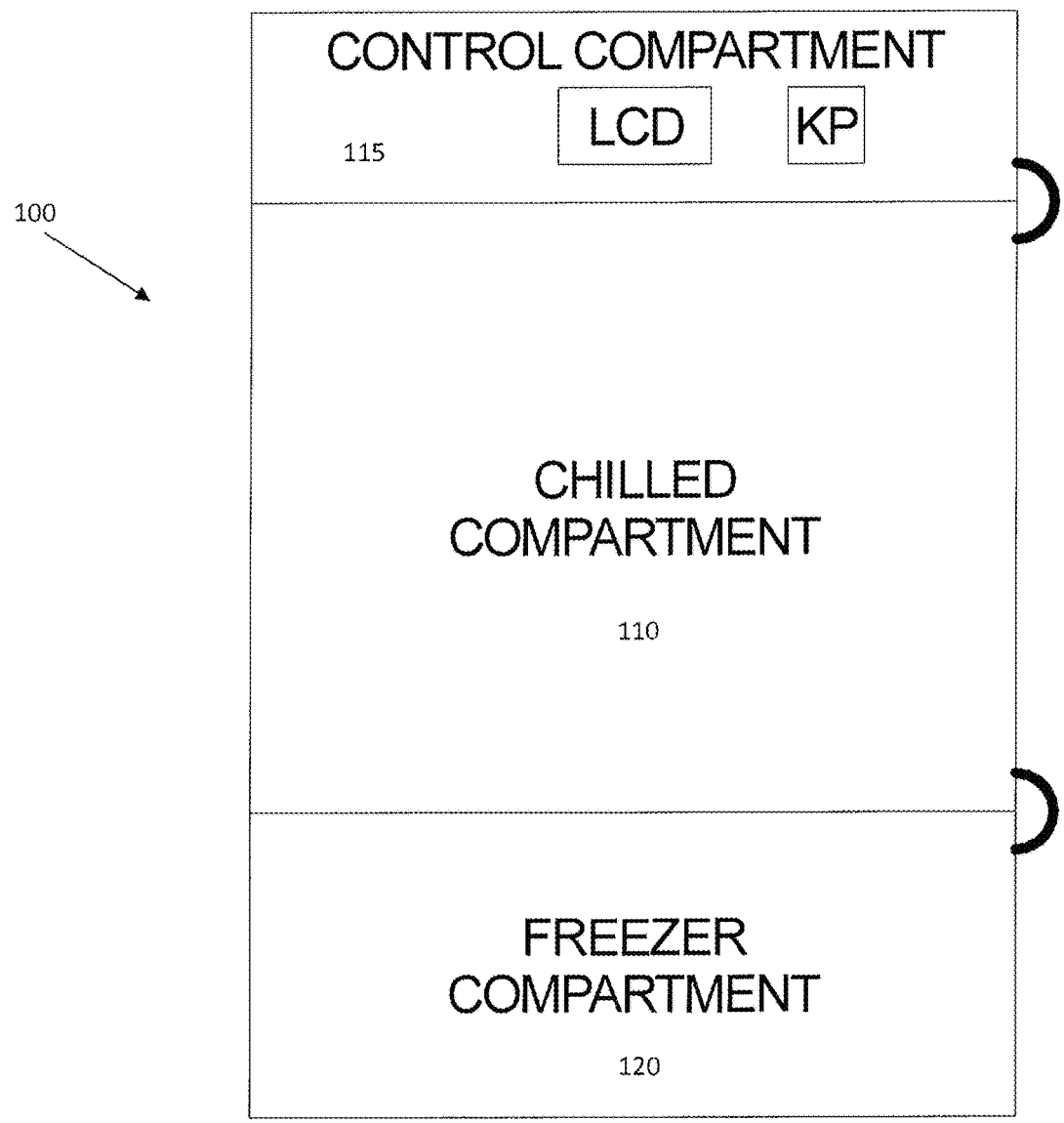
FIG. 1 is a schematic diagram of one embodiment of the present invention.

First, with reference to FIG. 1, an exemplary system according to certain aspects of an embodiment of the invention consists of a vending refrigerator 100, a communication interface, and a server. The system operates by a person removing a product from a chilled compartment 110 or a freezer compartment 120 in the vending refrigerator 100. A control compartment 115 records the transaction in its electronic system. Periodically the control compartment 115 uses the communication interface to send transaction data along with events (e.g., like historical temperature, power outage, alarms, etc.) to the server. The server then communicates with outside entities for inventory control, maintenance, alarms, billing, and any other essential tasks. A refill technician or specialist communicates with the vending refrigerator 100 using the display and keypad on the control compartment 115 or a web-enabled device to complete the refill cycle as more fully described below.

Figure 1A:
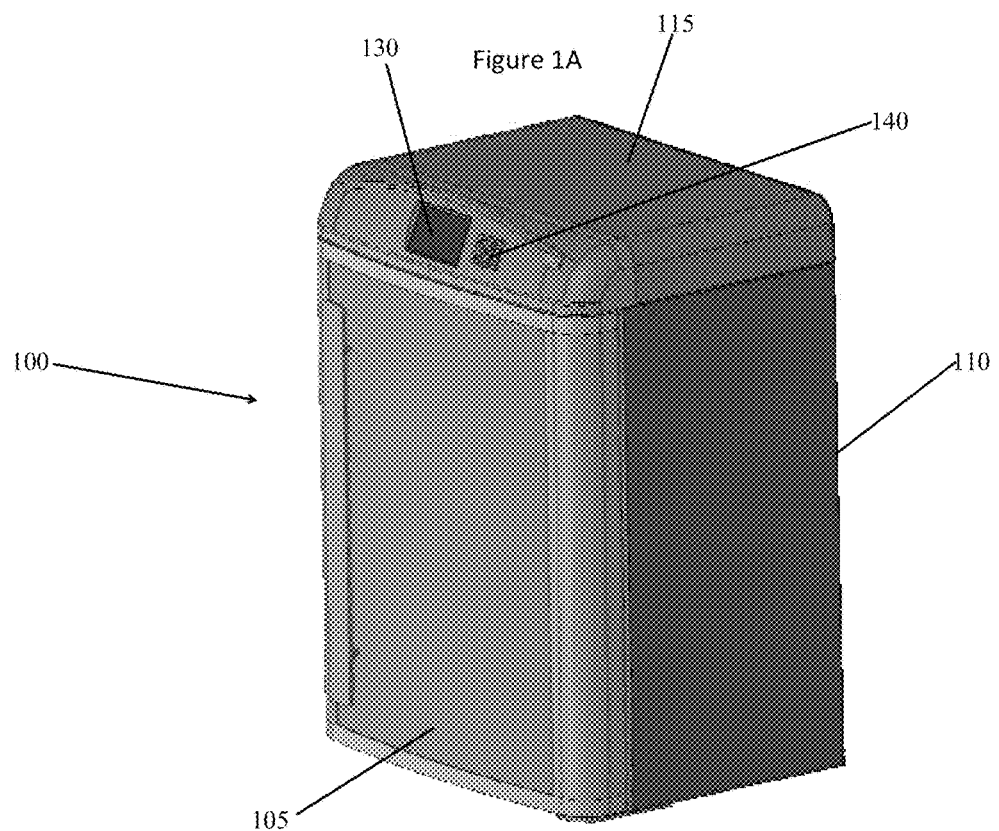
FIG. 1A is a front perspective view of a vending refrigerator.
Figure 1B:
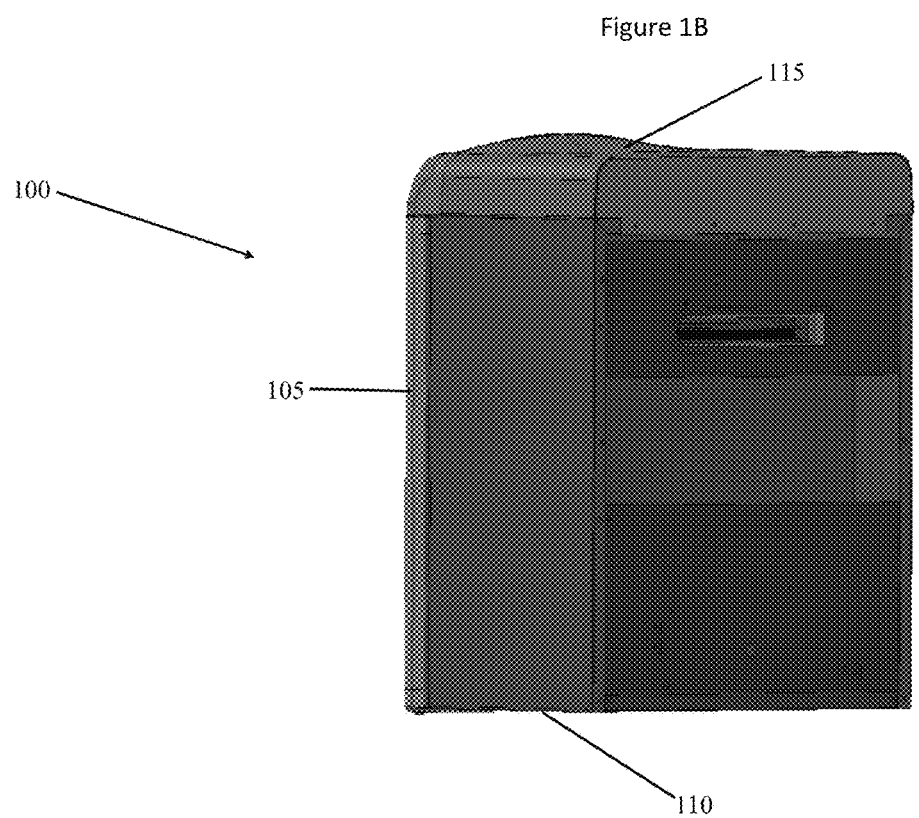
FIG. 1B is a rear perspective view of a vending refrigerator.

As shown in the block diagram of FIG. 1 and FIGS. 1A and 1B, a vending refrigerator 100, in accordance with certain aspects of an embodiment of the invention, generally comprises a chilled compartment 110, a door 105, and a control compartment 115. The external door 105 is provided an electric or mechanical lock, and is used to control access to the products stored in the vending refrigerator 100. If an electric lock is provided, such electric lock is preferably controlled by a processor platform in the control compartment 115 after a valid access code is entered or, as described more fully below, when specific events occur that require that the door be locked or unlocked.

The compartments are interconnected by a cabling system for communication and power.

Figure 1C:
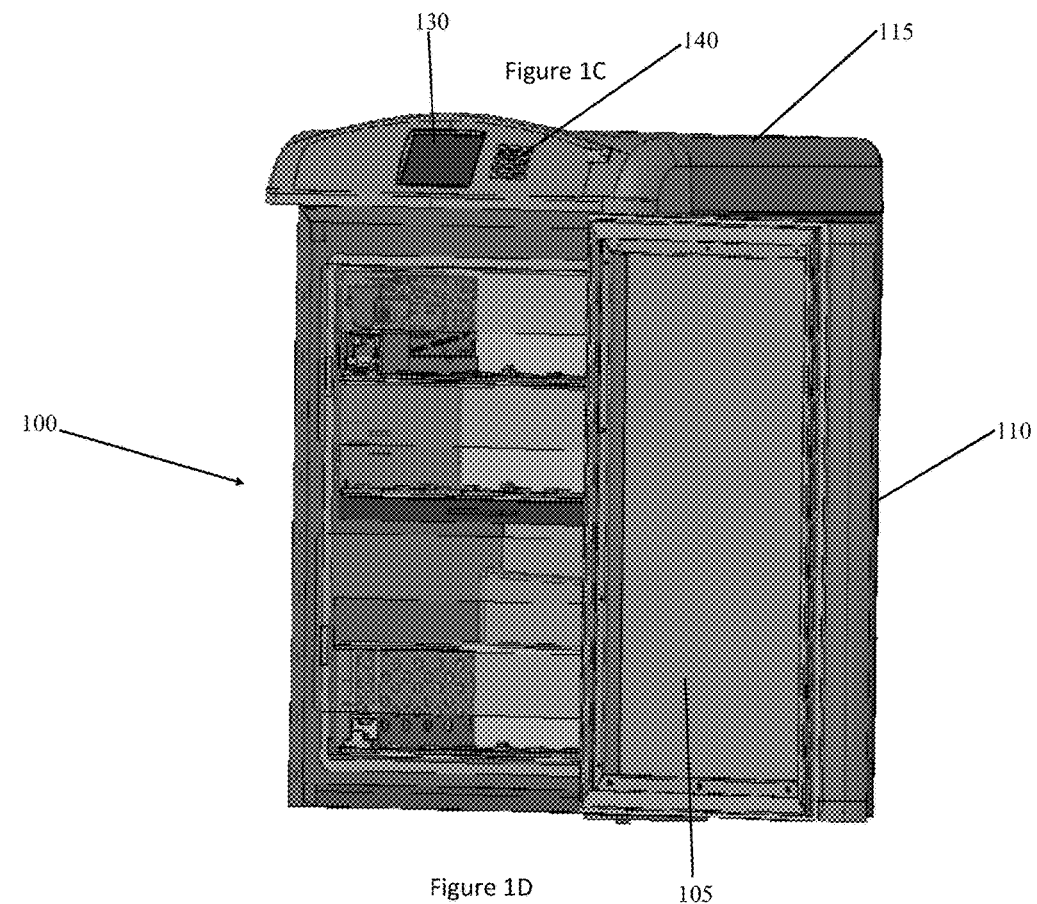
FIG. 1C is a perspective view of the vending refrigerator with its door open.
Figure 1D:
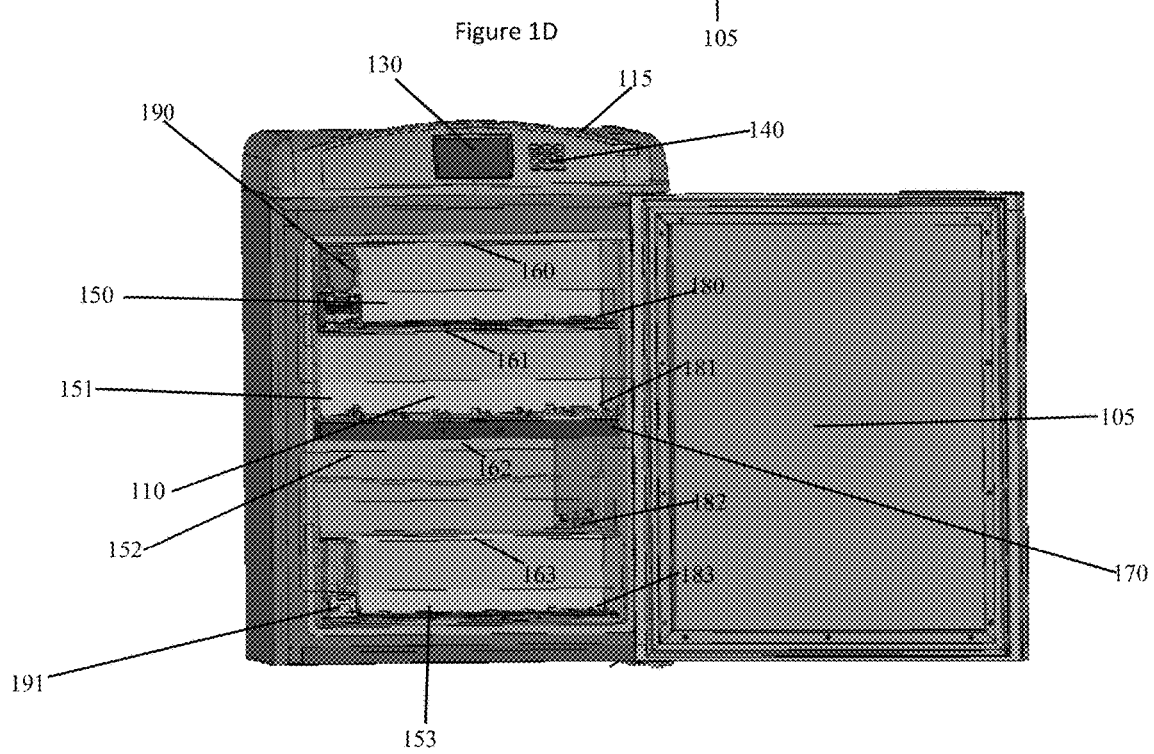
FIG. 1D is a front view of the vending refrigerator with its door open.

FIGS. 1C and 1D show the vending refrigerator 100 with its door 105 open. In some embodiments, the vending refrigerator 100 further comprises a freezer compartment 120. The vending refrigerator 100 requires only the control compartment 115 and the chilled compartment 110. The freezer compartment 120 is optional, and may be a plug-in add-on, but it can also be an integral part of the vending refrigerator 100. Optionally, the compartments may be stackable and can be stacked on an optional dry storage cabinet.

The control compartment 115 provides a user interface that a pharmacist, doctor, or other user may utilize to manage the vending refrigerator. In accordance with certain aspects of an embodiment of the invention, the control compartment 115 includes a display 130 and a user input device 140. The display 130 may consist of a LCD, and the user input device may be a key pad. Optionally, the user input device 140 and the display 130 may be combined into a touchscreen as will be recognized by a person of ordinary skill in the art. The control compartment 115 may also optionally include one or more of the following elements: an alarm sounder, a camera for a bar code reader, a USB communications interface, an external communications interface (Ethernet, PLC, POTS, Cellular, Satellite, WiFi, etc.), and an internal communications interface (I2C and GPIO) to the chilled compartment 110 and freezer compartment 120 (if installed), all controlled by a processor platform.

Figure 2:
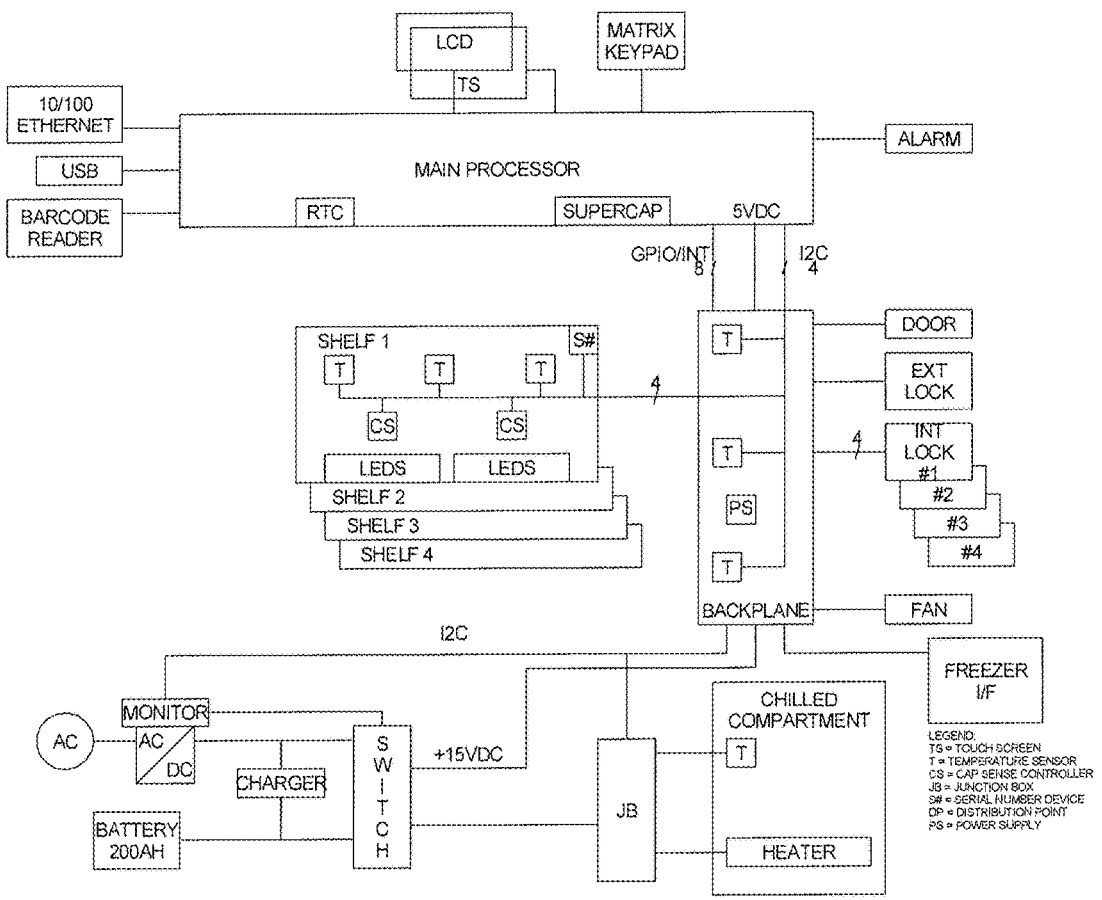
FIG. 2 is a block diagram of the control and chilled compartment.

The processor platform of the control compartment 115 includes a processor, memory, RTC, Battery Backup, and necessary interfaces to communicate with all hardware. The processor platform may use a Linux OS with an Android OS and application running on it, although alternative operating systems may be employed. FIG. 2 provides a schematic diagram of the electrical connections of an exemplary control compartment 115.

Preferably, all control and communications are handled by the control compartment 115. Users communicate with the vending refrigerator 100 via the user interface, e.g., keypad 140 and LCD 130, touchscreen, or web enabled device such as a smart phone, iPhone, tablet, etc. Communications to a server and external users are accomplished via the external communications interface. The user interface may be managed through a mobile device application to control the screens, touchscreen and keypad. The same mobile application or a remote website can be used in a mobile device and, thus, the user does not have to be located with the vending refrigerator 100 in order to affect such control. The mobile application or remote website enables any device available in the market to interact with the vending refrigerator 100 or the system that includes a vending refrigerator 100.

An alarm sounder is used to signify to local users that a critical event (no power, temperature out of range, etc.) has occurred and a user is needed to attend to the vending refrigerator 100. The user can mute the alarm via the LCD 130 and Touchscreen. A USB interface preferably provides a maintenance port for diagnostics and emergency download of data. It is contemplated that the interface may be any port, USB or otherwise, that allows physical electronic access to the vending refrigerator 100 components, e.g., Ethernet port, HDMI, etc. It can also be used to setup the vending refrigerator 100 and for manufacturing assistance. A barcode reader, which consists of a camera, camera interface, and an application to managing the reader, e.g., a mobile device or wireless device, can be used for reading data from the products to be stored in the chilled compartment 110 or freezer compartment 120. Typical data may include the kind of product, expiration date and lot code.

The main power supply is monitored to determine the type of current being supplied, e.g., AC or DC, the current voltage, and the current battery status. The interface is also used to control the switch between AC and a battery source for testing the battery and during loss of AC power. The switch is also used to shed the load of the chiller if the battery supply runs low. A backup power supply on the processor board consisting of a battery or supercap is used in the event that the main power source is not present. In the event that the main power source is not present, the software application will load the volatile data into non-volatile memory (Flash, MRAM, FRAM, EEPROM, etc.) using this backup power supply.

Internal communications with chilled compartment 110 and freezer compartment 120 may be handled via I2C of GPIO. The I2C is preferably used for the main communications for control and status. The GPIO is preferably used for real time interrupts and programming.

The chilled compartment 110 consists of an enclosure with or without a chiller (most preferably ammonia absorption, but in certain embodiments a compressor will be used). In accordance with certain aspects of an embodiment of the invention, and with particular reference to FIG. 1D, the chilled compartment 110 is divided into internal compartments 150, 151, 152, and 153 for product storage. Each storage compartment may include storage compartment doors 160, 161, 162, and 163. The storage compartment or internal doors 160, 161, 162, and 163 may include an electric or mechanical lock, and are used to hold the dispensers in place and to control access to the product dispensers' 190, 191 filling openings 320 (FIGS. 3A-3I), 415 (FIGS. 4A-4I). The doors 160, 161, 162, and 163 have access ports to the internal compartments 150, 151, 152, and 153 and dispensers 190, 191 to dispense product. The doors 160, 161, 162, and 163 are opened to gain access to the dispensers 190, 191 for refilling. The electric lock is controlled by the processor platform in the control compartment 115 and it can be opened after a valid access code is entered.

In some instances, one or more storage compartment doors may be joined. For example, as shown in FIG. 1D, storage compartment door 160 and 161 may be constructed as a single structure having a space for product dispensation. Similarly, storage compartment door 162 and 163 may be constructed as a single composition. The chilled compartment 110 may also include a temporary storage drawer 170. The temporary storage drawer 170 may be utilized to place product packages that were mistakenly removed from the dispenser compartments 190,191. This is to keep the product temperature in a safe condition until its eventual use. During a refill cycle the product will be reconciled.

With continued reference to FIG. 1D, each internal compartment 150, 151, 152, and 153 further comprises a dispensing shelf 180, 181, 182, and 183. All of the dispensing shelves 180, 181, 182, and 183 may have sensing capabilities as described more fully below. Optionally, one or more of the dispensing shelves (e.g., dispensing shelf 182) does not have sensing capabilities. Additional components of the chilled compartment 110 include temperature sensing elements, LEDs, electric locks, a door sensor, a fan, a processor controlled thermostat, and a power supply with UPS.

A backplane is located in the back of chilled compartment 110, and dispensing shelves 180, 181, 182, and 183 with sensing capabilities may be plugged into the backplane. The backplane buffers the communication signals between the sensing shelves 180, 181, 182, and 183 and the processor platform on the control compartment 115. Temperature sensors on the backplane are read by the processor platform similar to the temperature sensors on the sensing shelves. Controls for a fan and door locks are preferably located on the backplane and are in communication with the processor platform. The door sensor logic is preferably stored on the backplane for the processor platform to access. Control logic on the backplane may determine which shelf, device, or freezer interface the processor platform communicates with. Power from the main power supply is distributed on the backplane for the sensing shelves 180, 181, 182, and 183 and logic. Power is stepped down on the backplane for the processor platform in the control compartment 115.

One or more of the dispensing shelves 180, 182, 183, and 184 are configured to serve as docks for product dispensers 190, 191. The dispenser, e.g., 190, sits on top of a dispensing shelf, e.g., 180, with mechanical contacts to activate the sensors on the shelf (discussed in greater detail below). In accordance with certain aspects of an embodiment of the invention, the dispensing shelf, e.g., 180, has several sensor pads under each product dispenser 190, 191. The dispensing shelf 180 preferably has at least three sensor pads facing upwards in a configuration that allows product and drawer sensing as described in more detail below. The sensor pads are connected to a processor on the dispensing shelf 180 or directly to the processor platform on the control compartment 115 through the backplane. The sensors can be capacitive, infrared, or mechanical. A sensing application running on the processor detects the presence or absence of the product on that particular sensor. It can also detect the mechanical position of different parts of the dispenser. This data is sent to the processor platform in the control compartment 115 to determine if the product has been removed or if there is a malfunction. Data from a digital temperature sensor on the sensing shelf 180 is also sent to the processor platform in the control compartment 180 to be used in controlling a heater/cooler, for historical data for product aging, and for alarms.

Figure 3A:
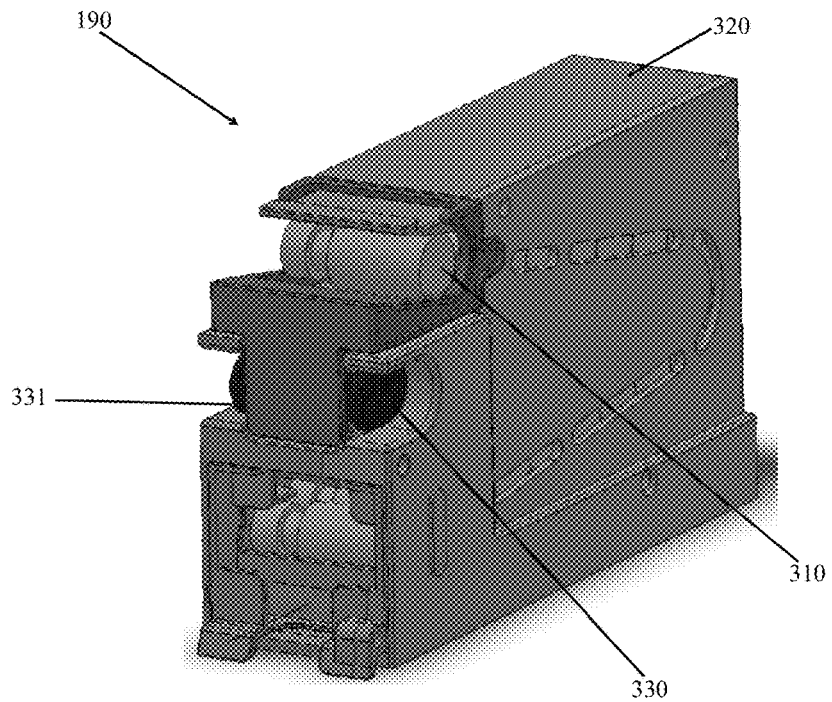
FIG. 3A is a perspective view of a first product dispenser.
Figure 3B:
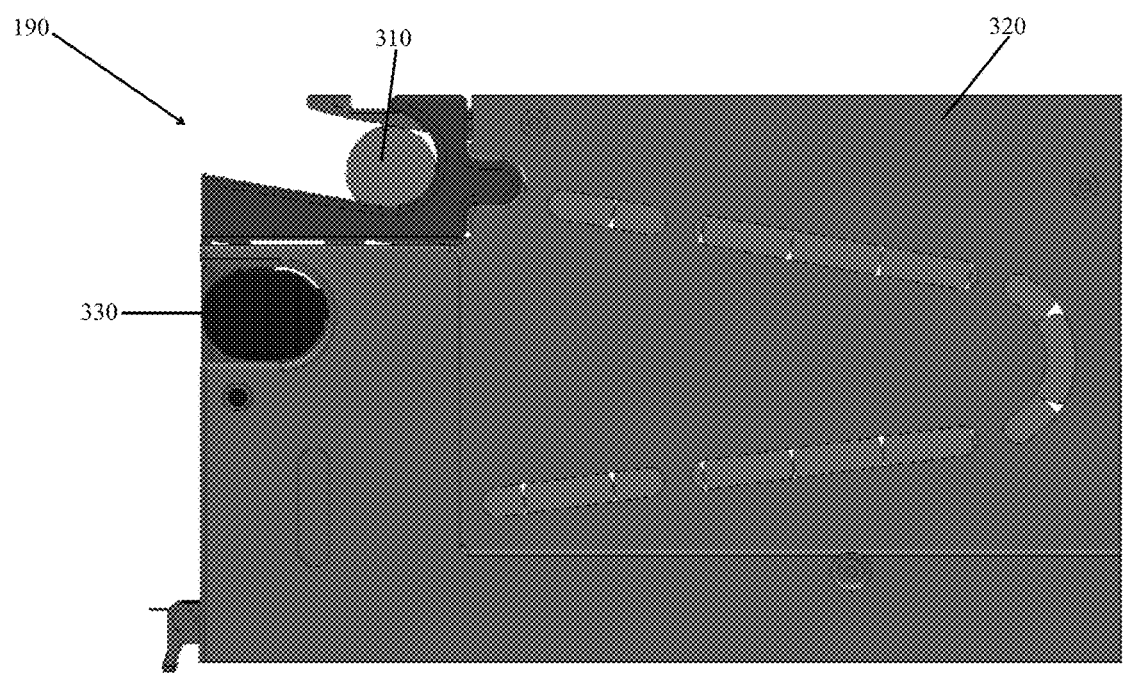
FIG. 3B is a left side view of a first product dispenser.
Figure 3C:
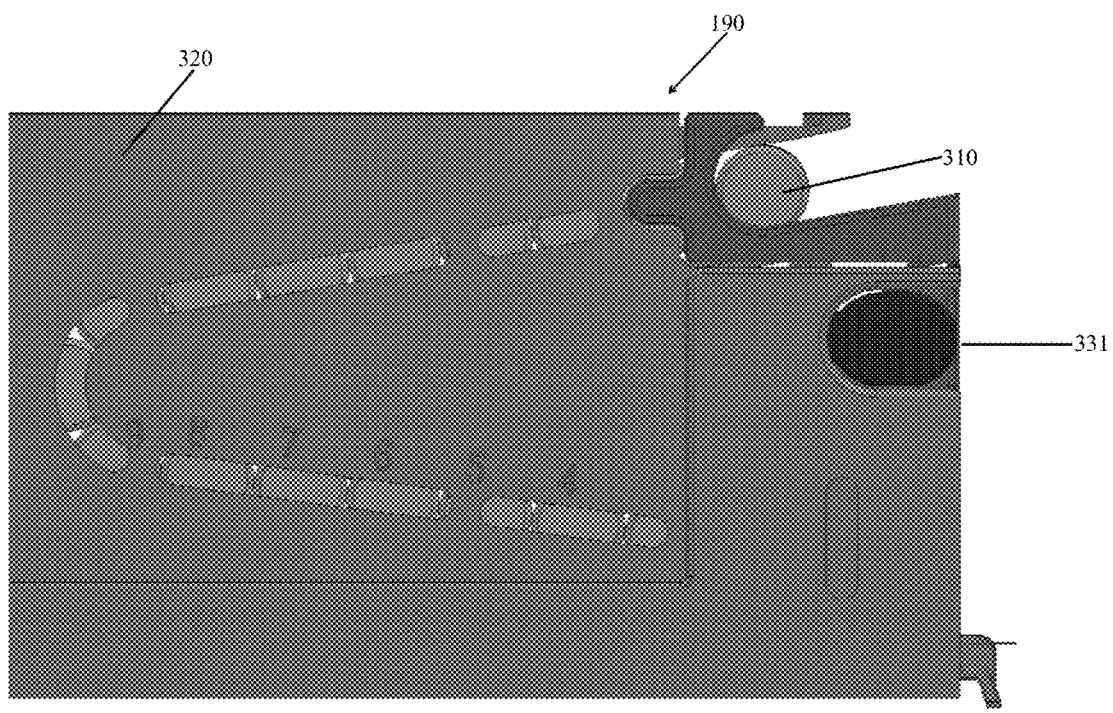
FIG. 3C is a right side view of a first product dispenser.
Figure 3D:
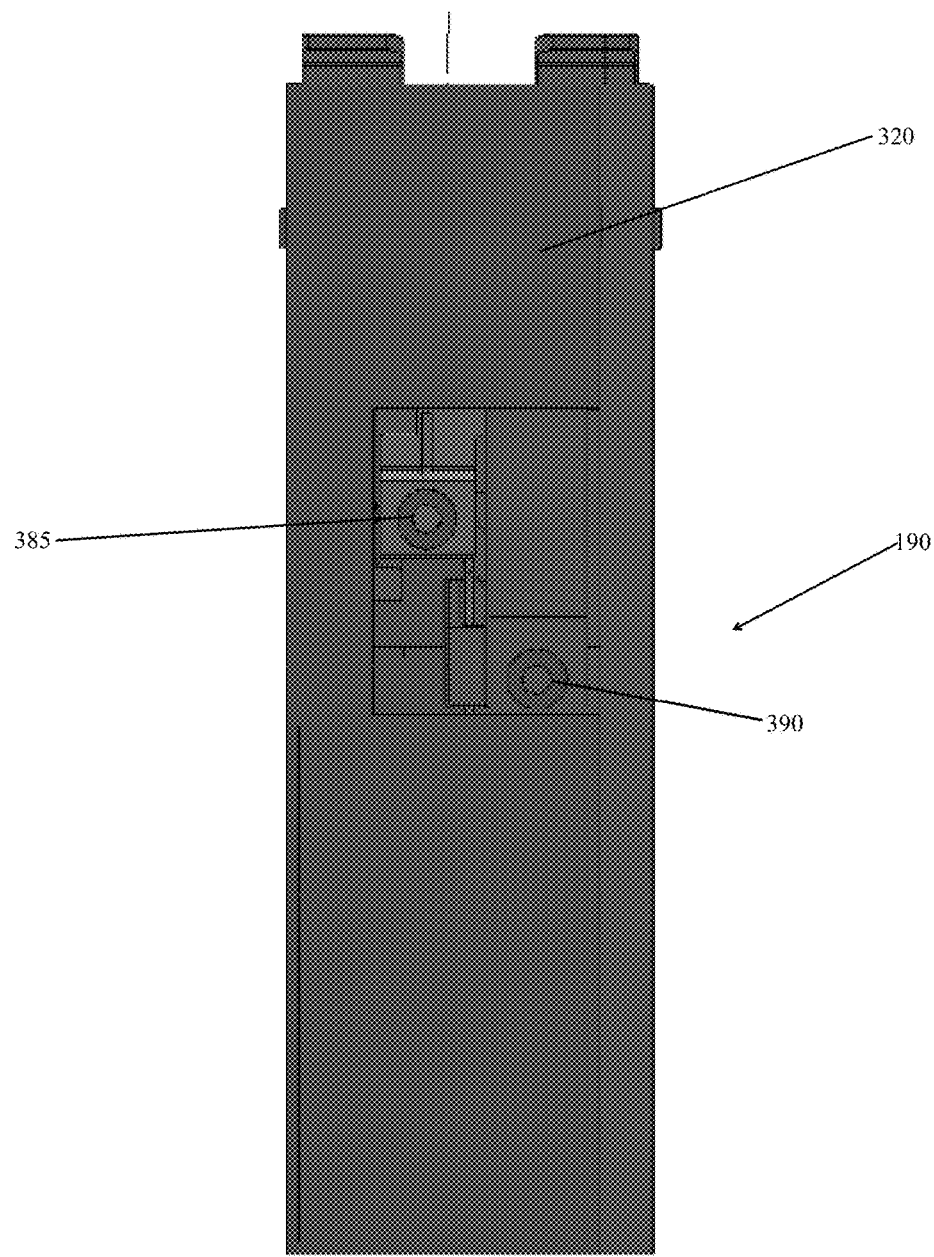
FIG. 3D is a bottom view of a first product dispenser.
Figure 3E:
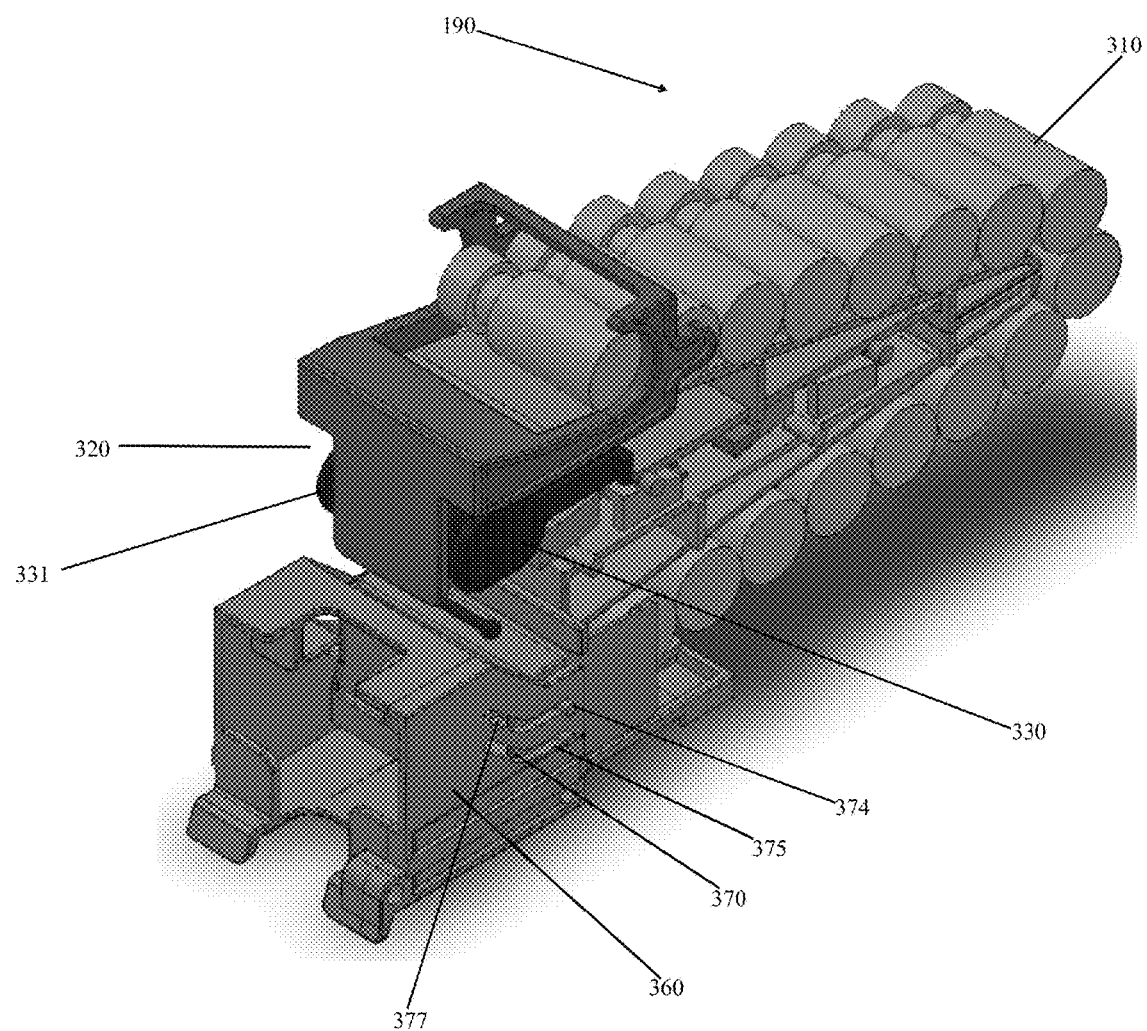
FIG. 3E is a perspective view of a first product dispenser without a cover.
Figure 3F:
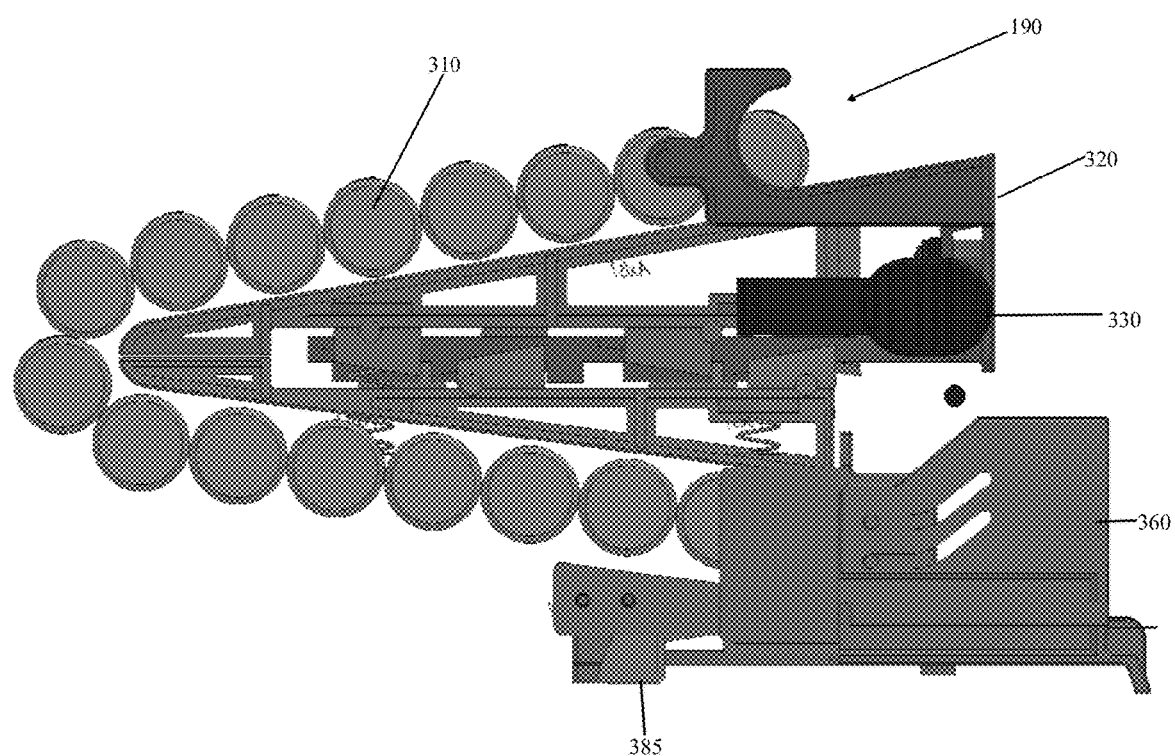
FIG. 3F is a right side view of a first product dispenser without a cover.
Figure 3G:
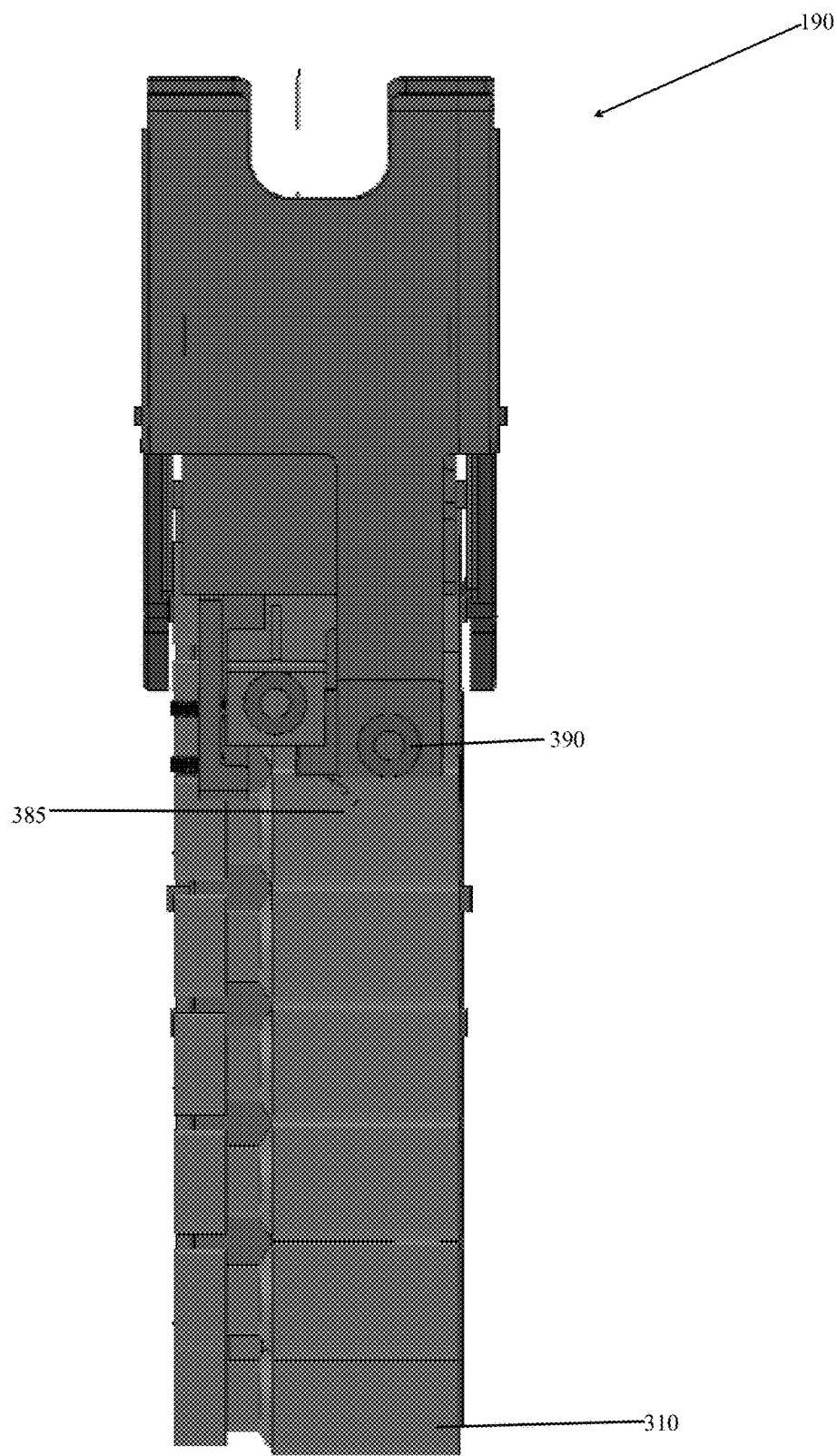
FIG. 3G is a bottom view of a first product dispenser without a cover.

A first product dispenser 190 with interchangeable ramps, as shown on FIGS. 3A through 3F, is used to dispense a first type of product package. The first product dispenser 190 may be configured to dispense vials 310. As used in this application, the term "vial" means a cylindrical container. In some instances, the vial may be a drug bottle with a cap. In other instances the vial may be a cylindrical container comprising a liquid that can be extracted by a syringe or poured out. In yet further instances, the vial 310 may be a medication tube or an ampule as recognized by a person of ordinary skill. FIGS. 3A through 3D show various views of the first product dispenser 190 that include the first product dispenser's cover 320. FIGS. 3D through 3F show the first product dispenser 190 without the dispenser cover 320. The first product dispenser 190 has a mechanism for refilling and dispensing a product contained in vials 310. The refill mechanism 320 is at the top of the first product dispenser 190 and is activated by squeezing the finger buttons 330, 331 and pulling the mechanism 320 towards the front of the first product dispenser 190. When the mechanism 320 is engaged, the internal springs 340, 341 apply pressure on the ramps 350, 351 so the first products 190 can be loaded properly. When the mechanism 320 is pushed back into the original position, the internal springs 340, 341 release the pressure on the ramps 351, 350 to let the vials 310 roll into position for dispensing.

In order to dispense a product, the user pulls on the dispenser drawer 360 at the bottom of the first product dispenser 190 and a product 310 is released into the dispenser drawer 360 for removal. The dispenser drawer 360 mechanism only allows one product 310 to be removed and will not allow the product 310 to be inserted into the first product dispenser 190 through the drawer. If the product 310 is left in the dispenser drawer 190 when open, the dispenser drawer 190 will not close, and, thus, the door 105 of vending refrigerator 100 will not close either. The internal ramps 350, 351 are interchangeable to allow for different vial sizes to be used in the first product dispenser 190.

Figure 3H:
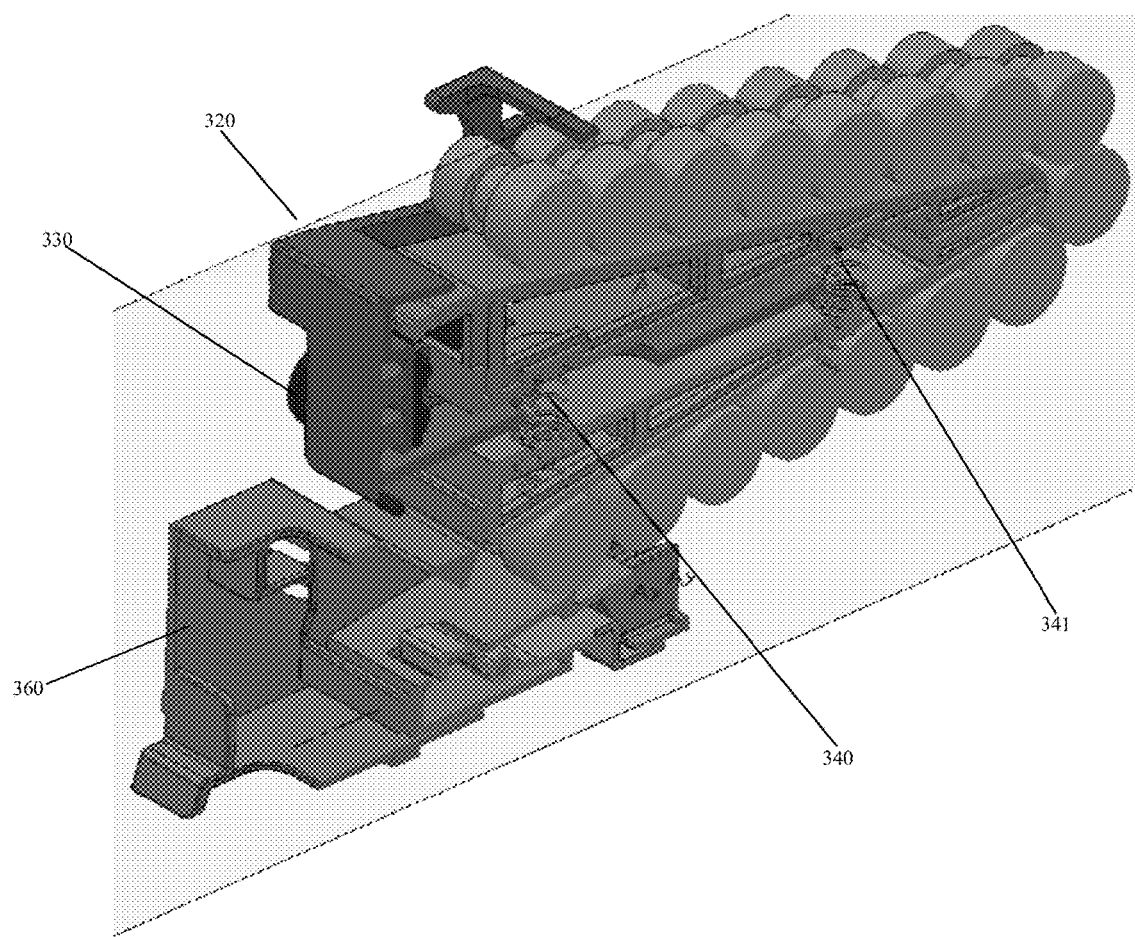
FIG. 3H is a perspective longitudinal cross-section of a first product dispenser.
Figure 31:
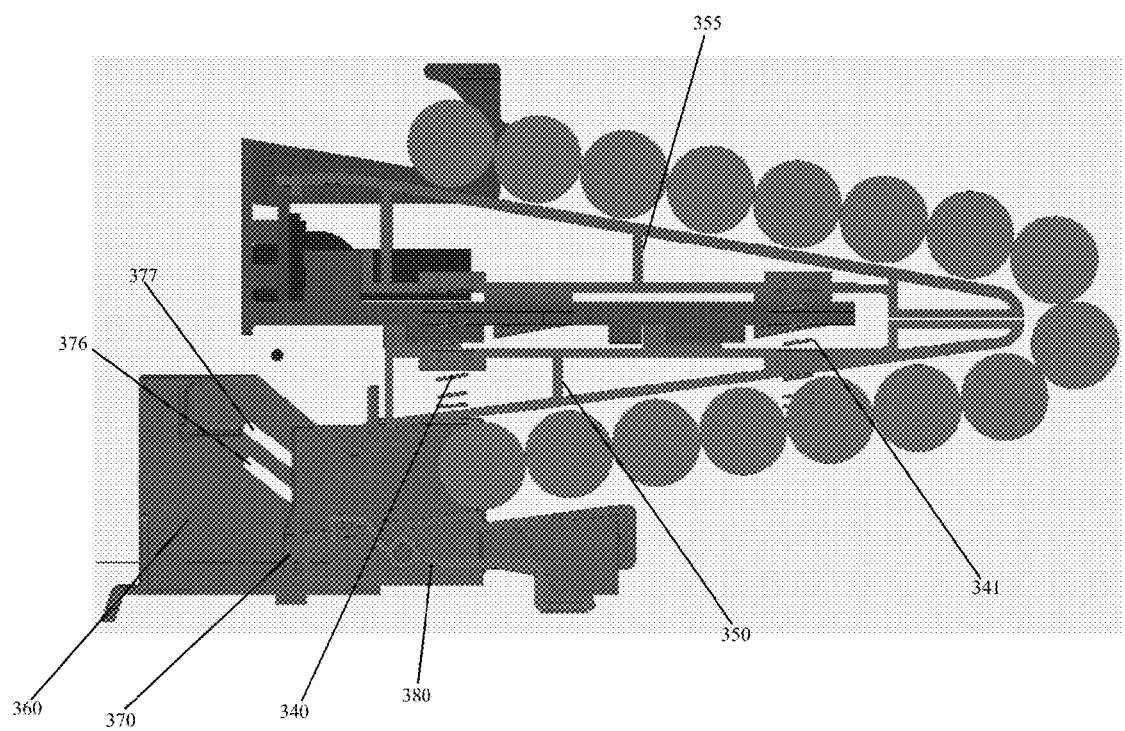
Figure 4A:
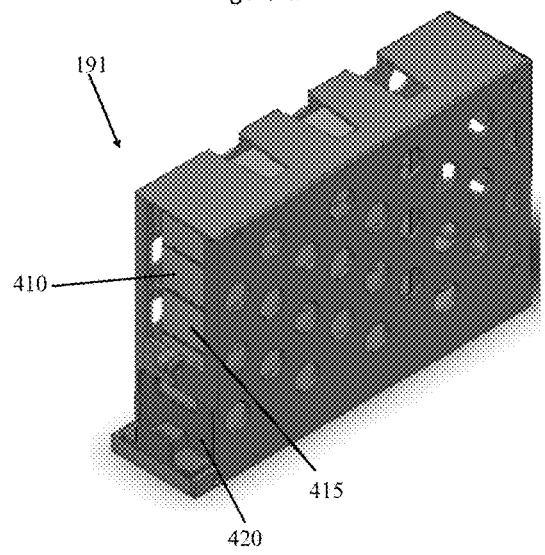
FIG. 4A is a perspective view of a second product dispenser with a closed drawer.
Figure 4B:
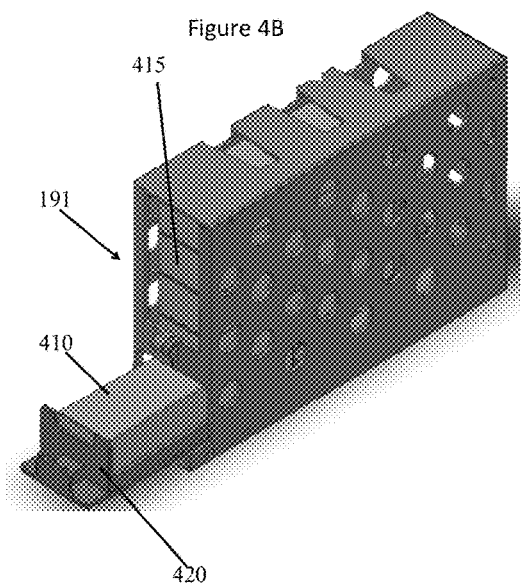
FIG. 4B is a perspective view of the second product dispenser with the drawer partly open.
Figure 4C:
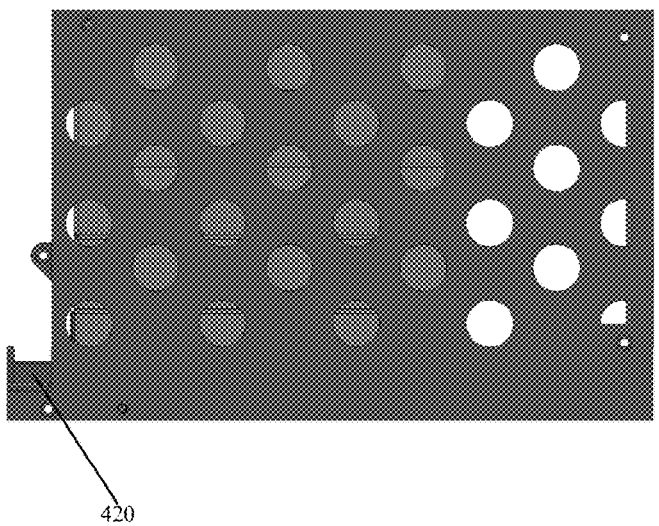
FIG. 4C is a left side view of the second product dispenser with a closed drawer.
Figure 4D:
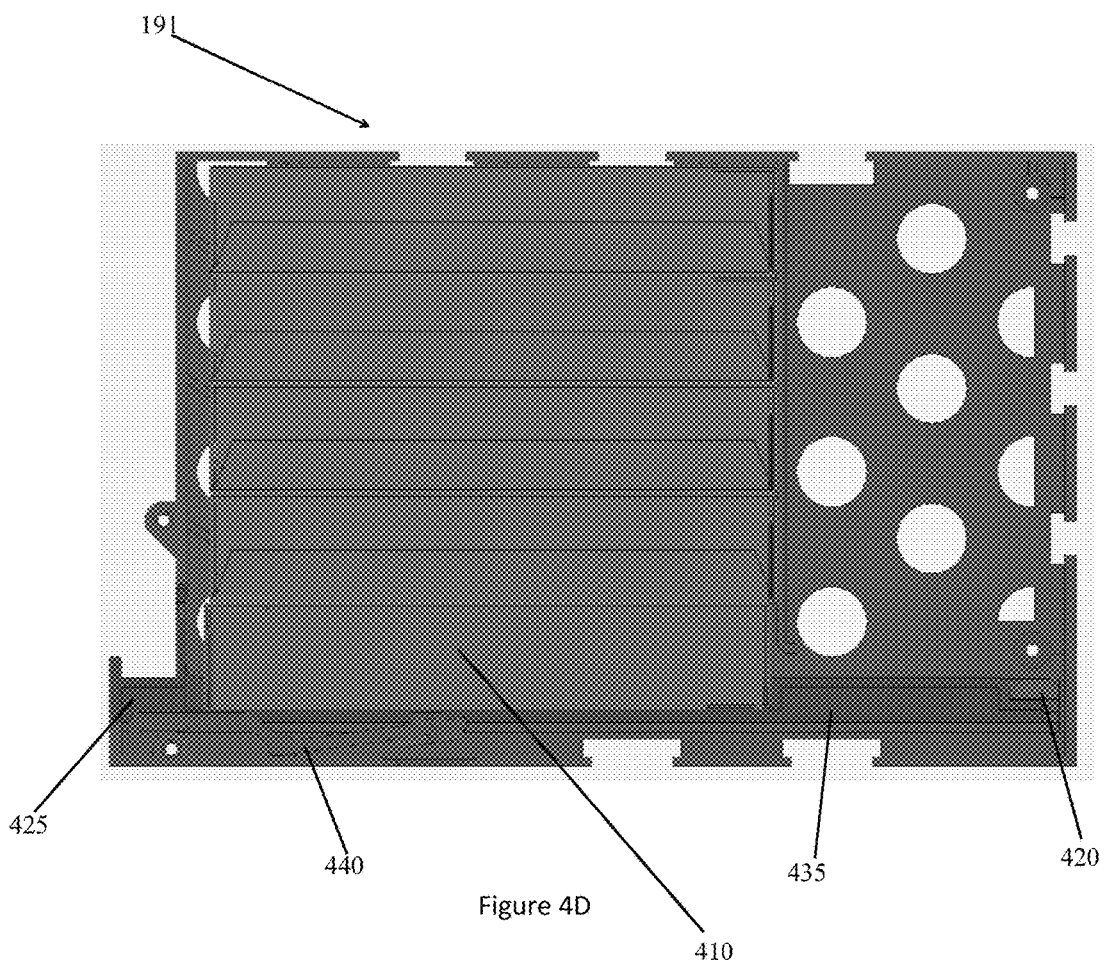
FIG. 4D is a left side cross-sectional view of the second product dispenser with a closed drawer.
Figure 4E:
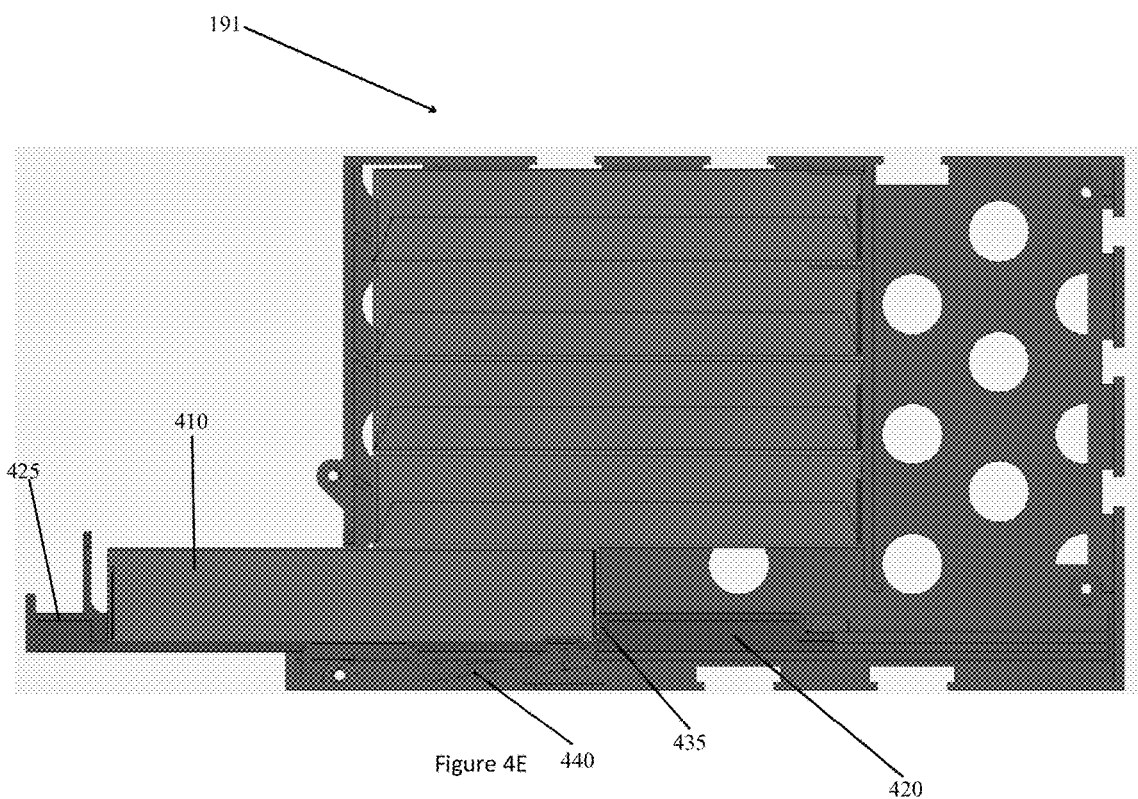
FIG. 4E is a left side cross-sectional view of the second product dispenser with the drawer partly open.
Figure 4F:
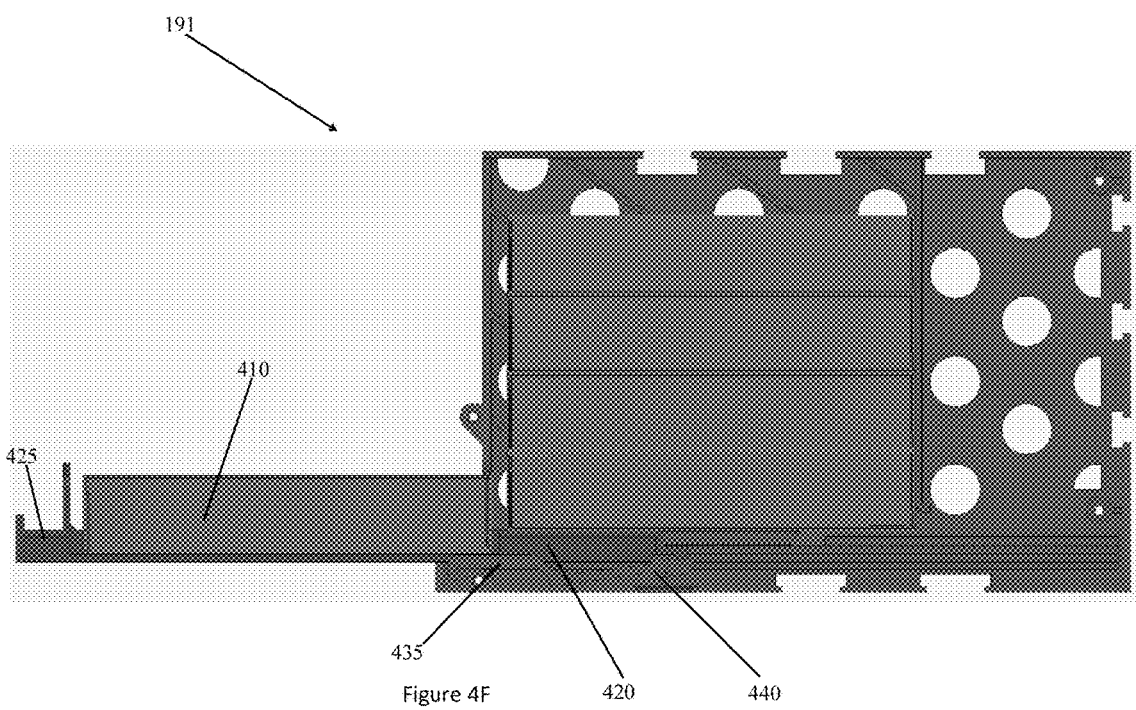
FIG. 4F is a left side cross-sectional view of the second product dispenser with the drawer fully open.
Figure 4G:
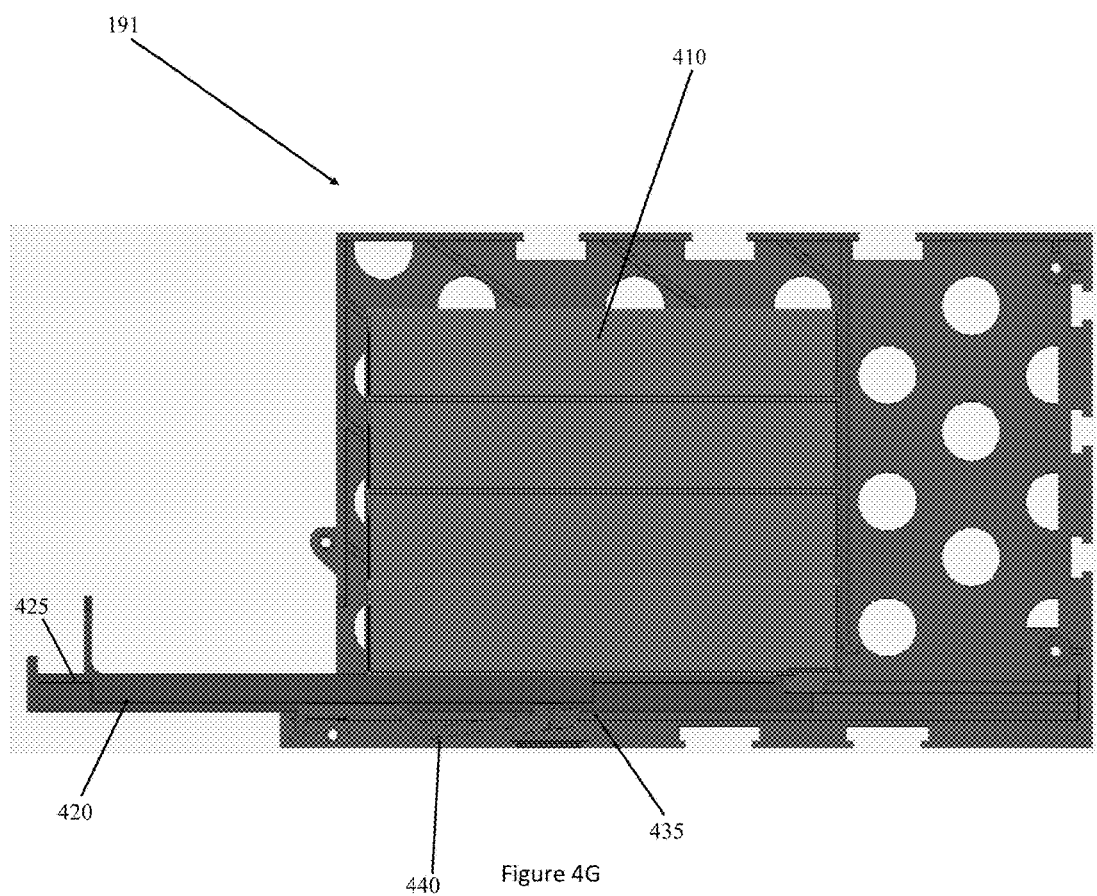
FIG. 4G is a left side cross-sectional view of the second product dispenser with the drawer fully open and the box removed.

FIGS. 3H and 3I show the open (3H) and closed (3I) configurations of the first product dispenser 190. When the dispenser drawer 360 is closed, a guard 370 is up, preventing vials 310 from exiting the dispenser drawer 360 compartment. Two notches 374, 375 (shown in FIG. 3E) ride along guides 376, 377 on the dispenser drawer 360 raising the guard 370 when the dispenser drawer 360 is closed and lowering the guard 370 when the dispensing drawer 360 is open allowing the vial 310 to exit. The first product dispenser 190 also includes a sensing lever 380 that includes a vial sensor 385. When the dispenser drawer 360 is closed and there are vials 310 in the first product dispenser 190, the next vial 310 for dispensing pushes the front end of the sensing lever 380 down causing the rear end of the sensing lever 380 to rise breaking the connection between the vial sensor 385 and a dispensing shelf 180 sensor indicating that there is a vial 310 in ready to be dispensed. When the dispensing drawer 360 is open and there are no vials 310 pressing the front end of the sensing lever 380, the rear end of the sensing lever 380 is lowered and connects the vial sensor 385 with the sensor on the dispensing shelf 180, indicating that there is no vial 310 in line to be dispensed. When the first product dispenser drawer 360 is closed, the next vial 310 in line moves forward, pushing down the front end of the sensing lever 380 and causing the rear end of the vial sensor 385 to rise and lose its connection with the sensor on the dispensing shelf 180. It is contemplated that other sensor configurations could be readily implemented by a person of ordinary skill in the art.

A drawer position sensor 390 is located on the bottom of the dispenser drawer 360. The drawer position sensor 390 connects with a closed position sensor on the dispensing shelf when the dispenser drawer 360 is closed, indicating to the processor platform in the control compartment 115 that the dispenser drawer 360 is closed. The drawer position sensor 390 connects with an open position sensor on the dispensing shelf 180 when the dispenser drawer 360 is fully open, indicating to the processor platform in the control compartment 115 that the dispenser drawer 360 is fully open.

A second product dispenser 191 is used to dispense products that are packaged in square or rectangular boxes, such as pre-filled syringes packaged in a custom cardboard box 410 as shown in FIGS. 4A through 4I. A preferred embodiment consists of cardboard boxes 410 containing syringes, but a person of ordinary skill in the art would understand that any type of medication or product may be packaged and dispensed in boxes 410 that fit the dispenser 191. The boxes 410 are loaded into the dispenser 191 through an opening 415 in the front of the dispenser 191. A second product dispenser drawer 420 at the bottom of the dispenser 191 is pulled out towards the front to remove a box 410. Once the drawer 420 is fully extended, the drawer 420 will not close until the box 410 is removed. The empty drawer 420 can be pushed back into the dispenser 191 and a new box 410 will drop into the drawer 420. This prevents a box 410 from being inserted back into the dispenser 191 through the drawer 420.

FIGS. 4D through 4G show a cross-section of the dispenser 191. The drawer 420 comprises a front end 425 with a handle that allows a user to pull and push the drawer 420. The drawer also includes a tray section 430 designed to fit a specific size of box. A person of ordinary skill would understand that various types of tray sections 430 can be provided in different drawer 420 configurations. The drawer 420 also includes a rear section 435. The rear section 435 is higher than the tray section 430 and serves two functions. First, it pushes the box 410 as the user pulls the drawer 420 handle. Second, it supports a second box 410 that drops onto this rear section 435 once the first box 410 has cleared the front end of the dispenser 191 and has been removed. When the empty drawer 420 is pushed back into place the second box 410 drops onto the tray section 430.

The second product dispenser 191 includes a sensing lever 440, similar to the sensing lever 380 of the first product dispenser 190. The rear section of the sensing lever 440 has a sensing element 445, which connects with a sensor on the dispensing shelf 183 when there are no boxes on the drawer 420 or when the drawer is pulled out and a new box 410 is sitting on the rear section 435 of the drawer. As shown in FIG. 4I, the drawer has a channel 450 that allows the sensing lever 440 to rise above the plane of the tray section 430 when a box 410 is not in the tray section 410. This allows the rear section of the sensing lever 440 to drop and make contact with a sensor on the dispensing shelf 183.

A drawer position sensor 490 is located on the bottom of the dispenser drawer 420. The drawer position sensor 490 connects with a closed position sensor on the dispensing shelf 183 when the dispenser drawer 420 is closed, indicating to the processor platform in the control compartment 115 that the dispenser drawer 420 is closed. The drawer position sensor 490 connects with an open position sensor on the dispensing shelf 183 when the dispenser drawer 420 is fully open, indicating to the processor platform in the control compartment 115 that the dispenser drawer 420 is fully open.

With reference again to FIG. 1D, the vending refrigerator 100 also includes an internal compartment 151 to be used as a temporary storage compartment. It is contemplated that any of the internal compartments 150, 151, 152, 153 can be used as the temporary storage compartment. The temporary storage compartment is used to place products 310, 410 from either product dispensers 190, 191, which were mistakenly removed or if they contain multiple doses. The temporary storage compartment may be formed by a third dispensing shelf 182 in the vending refrigerator. The third dispensing shelf may or may not have any sensors on it. It is also contemplated that the vending refrigerator 100 may include multiple compartments without product dispensers 190, 191, that may be used as temporary storage compartments.

A junction box may control a heater for an ammonia absorption chiller or the compressor for maintaining a constant temperature in the chilled compartment 110 (or a compressor for the freezer compartment 120 discussed below). The junction box consists of a processor, SSR or SCR, I2C communication interface, NTC temperature probe, and power supply. If the chiller is ammonia absorption, the processor runs a standard PID algorithm and numeral-impulse control with modifications for over temperature. The over temperature function is to shut down the heater when it appears the chiller is overheating due to low gas, bad heater, or high current. The nominal temperature setting for the inside of the chilled compartment 115 will be controlled by the processor platform communicating with the junction box. Current status of the junction box is read by the processor platform in the control compartment 115.

An AC/DC power supply with line filter is preferably used to provide a stable voltage for all of the electronics. The output of the power supply is used to charge a backup battery. Both the output of the power supply and the backup battery are controlled by a power switch. The power switch is controlled by the processor platform in the control compartment 115 for selecting how the electronics and the chilled compartment 115 will be powered. The processor platform monitors the main power supply and backup battery via the I2C communications interface.

Figure 5:
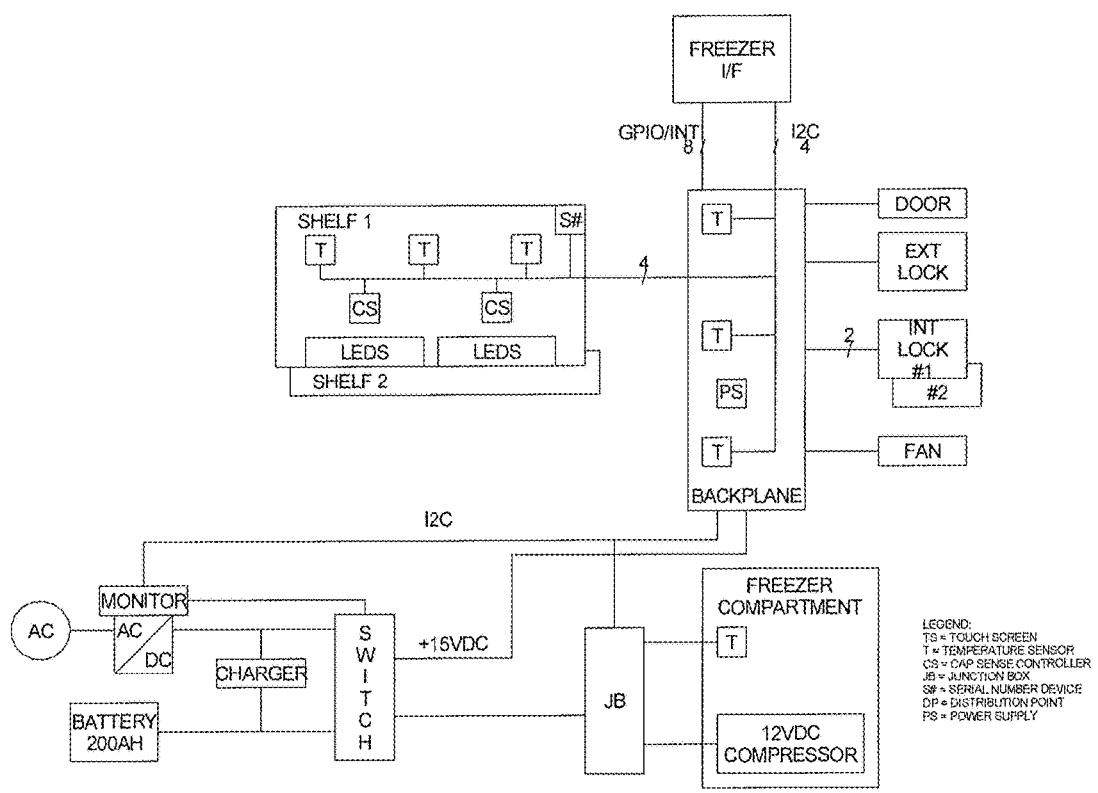
FIG. 5 is a block diagram of the freezer compartment.

In accordance with certain aspects of an embodiment of the invention, where a freezer compartment 120 is used, the freezer compartment 120 preferably includes an enclosure with a compressor chiller, compartments for holding product dispensers, one or more doors for storage compartments, a temporary storage drawer, dispensing sensing shelves, temperature sensing, LEDs, electric locks, a door sensor, a fan, a processor controlled thermostat, a power supply with UPS, and a communication link to chilled compartment 110 or the control compartment 115, as shown in FIG. 5. The freezer compartment preferably includes a freezer interface that contains I2C and GPIO signals necessary for communications with the processor platform in the control compartment 115. These signals are buffered and sent to the processor platform through the backplane. It is contemplated that the freezer compartment 120 is configured in the same way as the chilled compartment and includes the same features, except that its temperature can be set below freezing to maintain products at lower temperatures than in the chilled compartment 110.

The temporary storage drawer is to be used when a product is inadvertently dispensed. This is to keep the product temperature in a safe condition until its eventual use. During a refill cycle the product will be reconciled.

All control and communications are preferably handled by the control compartment 115. The vending refrigerator may be configured to communicate with a server. In this configuration, the server consists of a computer running application software that is located at an off-site facility. This application software processes incoming data from the vending refrigerator 100 and generates the data necessary for inventory control, maintenance, alarms, billing, and any other essential tasks. The data is also used to dispatch personnel for maintenance, customer support for alarms, and refilling.

Figure 6:
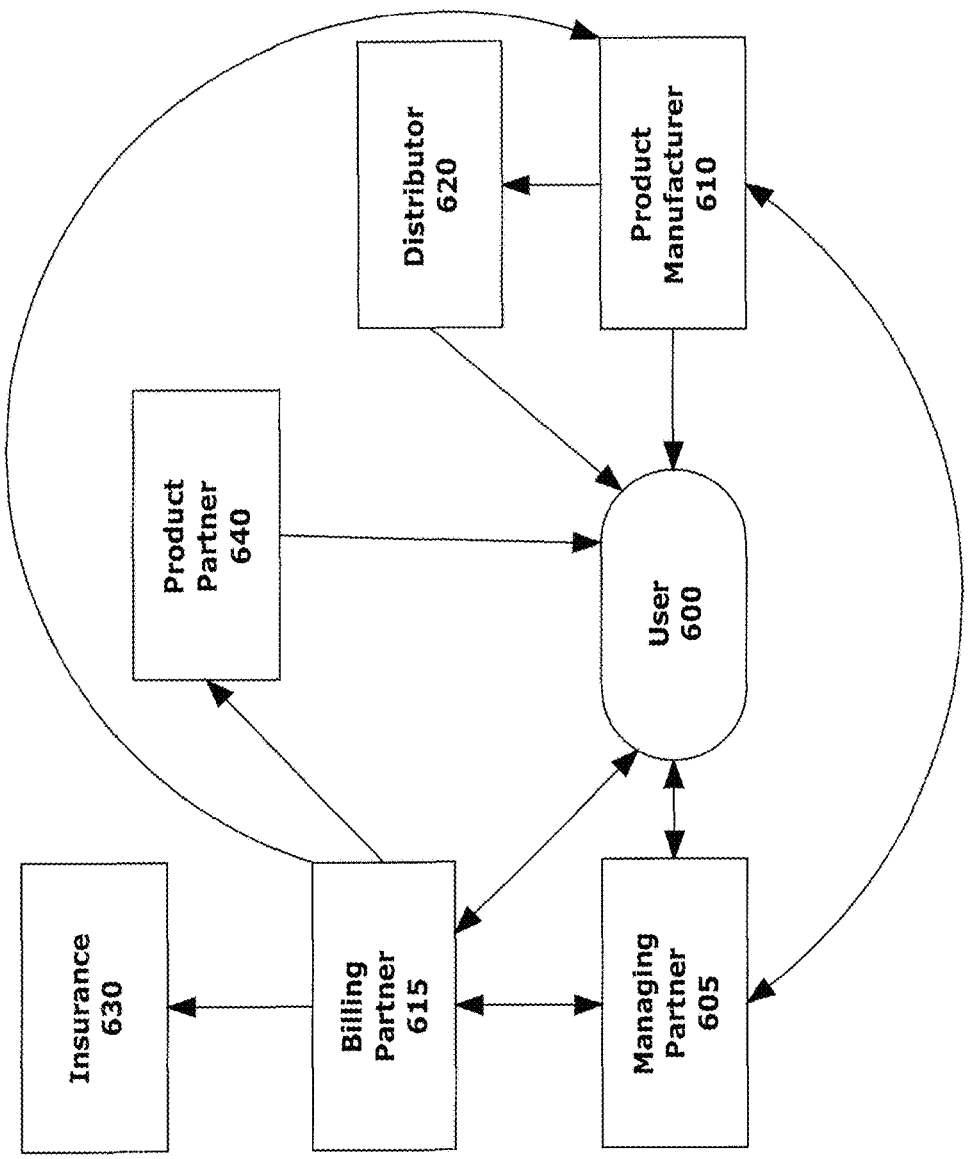
FIG. 6 is a schematic diagram of a system in accordance with one embodiment of the vending refrigerator.

The server and refrigeration unit may communicate with one another, and form part of a fully integrated product supply, storage, and distribution system, as further described below, and as shown schematically in the exemplary flow diagram shown in FIG. 6.

The first element of the system is a user facility 600. The user facility 600 is where the vending refrigerator 100 is placed. It may be a physician's office, but it could be any other place where the vending refrigerator 100 is to be used, e.g., a pharmacy, a health department office, etc. Another element of the system is a product manufacturer 610, such as a company that manufactures the products that are to be dispensed through the vending refrigerator. An optional element of the system is a distributor 620, which is used by the manufacturer 610 to deliver the product to the user 600. A product partner 640 may also be provided that has the responsibility of managing the inventory of product in the vending refrigerator 100. A managing partner 605 may be used in certain instances to control the functions of the vending refrigerator 100. In some instances, the managing partner 605 is the manufacturer of the vending refrigerator 100 and has responsibility for maintenance of the equipment and the data collected from the vending refrigerator 100. A billing partner 615 is responsible for invoicing and settling accounts with the various other members of the system. Insurance 630 may be another component, which is in communication with the billing partner 615 to manage payment for spent product.

Figure 7:
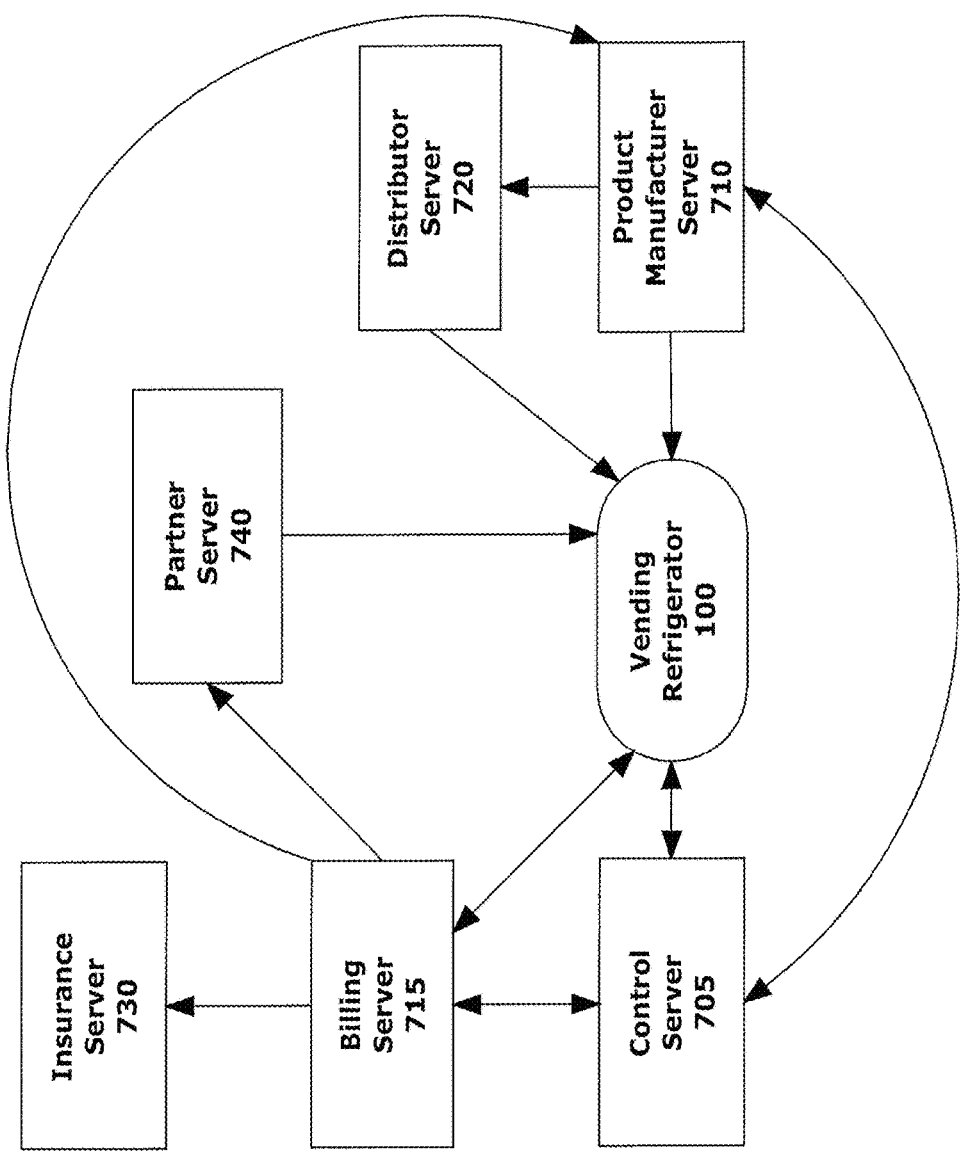
FIG. 7 is a schematic diagram of a network for implementing a system in accordance with one embodiment of the present invention.

The system is implemented through an integrated network as shown in FIG. 7. In accordance with certain aspects of an embodiment of the invention, the vending refrigerator 100 is communicatively connected with the control server 705 at the managing partner 605, the product manufacturer server 710, the distributor server 720, the partner server 740, the billing server 715, and the insurance server 730. A person of ordinary skill in the art will recognize that the vending refrigerator need not be connected to all of the components listed above. For example, the vending refrigerator 100 may be connected to the control server 705 and the control server 705 may be used to communicate with all other components as necessary.

The system described above is used to implement a method for distribution and dispensing of products. A product is first delivered to the user 600 from the manufacturer 610 or distributor 620. Data is collected from the control compartment 115 on the contents and operation of the vending refrigerator 100 and sent to the control server 705. The control server 705 handles all transactions concerning the products dispensed through the vending refrigerator 100. All data including alarms from the vending refrigerator 100 are sent and processed by the control server 705. The control server 705 processes the data and determines whether the vending refrigerator 100 needs to be refilled or if maintenance is required.

Optionally, a billing server 715 at the billing partner 615 may receive information directly from the vending refrigerator 100 or the control server 705. The billing server 715 manages billing to and from user 600, billing to and from insurance company 630, and orders stock from the product manufacturer 610. The billing server 715 may also schedule visits from a product partner 640 to go to the user 600, while coordinating with the delivery of the product. The product partner 640 may be an organization with individuals qualified to store and maintain the physician's vaccine stock. In such instances, the product partner 640 preferably uses a CDC vaccine handling document in establishment of procedures. When a patient receives a vaccine, or other medication dispensed through the vending refrigerator 100, the information is sent from a scanned vial or extracted from the POMIS (Physician's Office Management and Medical Information System) to the billing server 715 to bill the insurance company 630 for the patient to whom the product was provided.

The control server 705 will send stock refill requests to the billing server 715 when stock levels fall below pre-determined amounts. The billing server 715 needs to place such orders in a timely manner to ensure that the physician's office does not run out of any medication, e.g., a vaccine. The control server 705 will track all on-hand inventory. The billing server 715 will track all orders for deliveries and provide delivery information to the control server 705. All alarms from the vending refrigerator 100 in the physician's office will be sent via control server 705 to the billing server 715 for notification. Insurance 630 refers to entities that reimburse the product partner 640 for the cost of the drug, e.g., a vaccine, and reimburse the physician for administering the drug. Billing server 715 will bill the insurance company 630 and dealing with managing the insurance payment transaction.

Manufacturer 610 refers to entities that are going to supply medications, e.g., vaccines, to the user 600 or product partner 640. The manufacturer 610 receives at product manufacturer server 710 an order from the billing server 715. The order is then shipped directly to the user 600 or product partner 640 with the tracking number and manifest sent to the billing server 715, which will relay that information to the control server 705. It is contemplated that the medications will arrive in a timely manner, e.g., within 48 hours of shipment.

Figure 8:
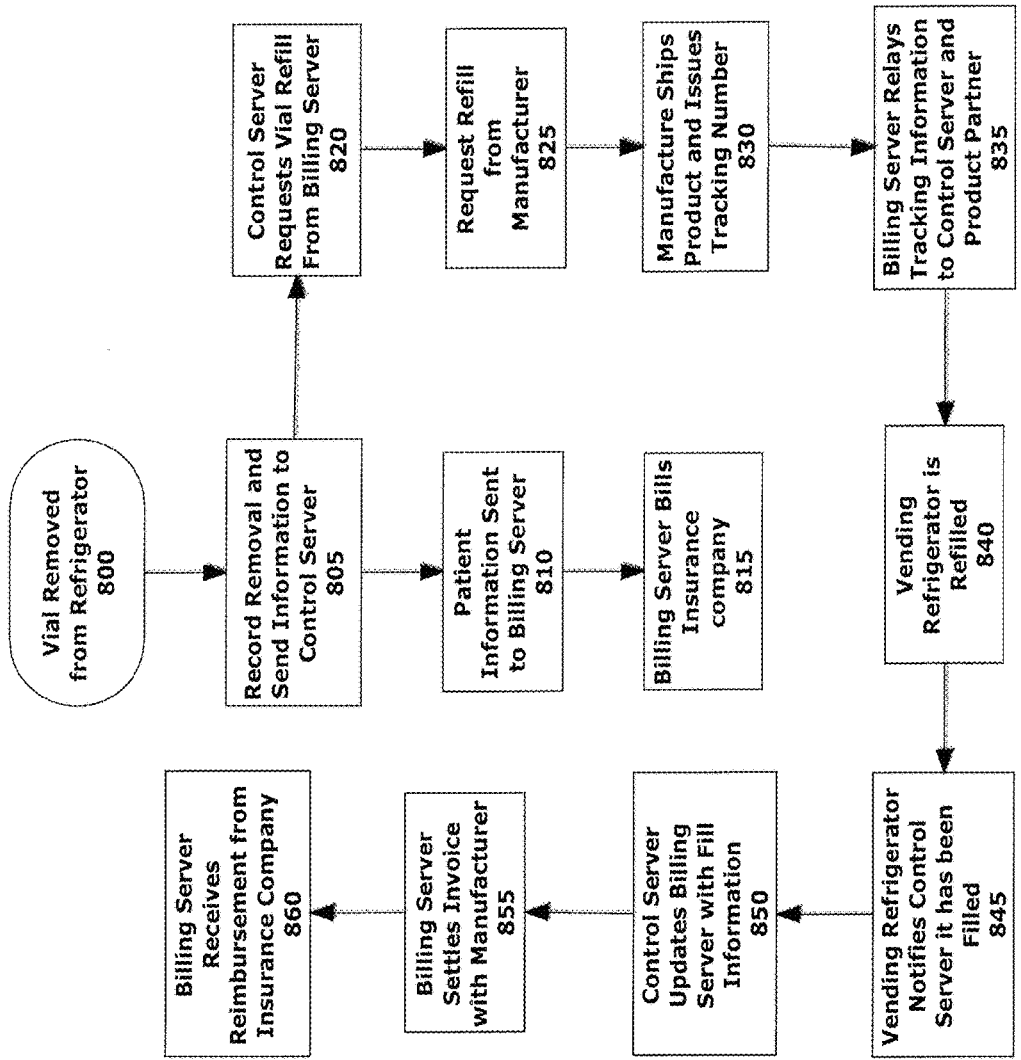
FIG. 8 is a flow diagram of a process for dispensing products from the vending refrigerator.

One exemplary method in accordance with an embodiment is provided in FIG. 8. In a first step 800, an operator, such as a nurse in the physician office 600, removes a vial from the vending refrigerator 100. In a second step 805, the vending refrigerator 100 records the removal and sends the information to control server 705. In a third step 810, the nurse enters the information in the patient record and the data is sent to the billing server 715 for billing by extracting the relevant information from the POMIS. In the next step 815, the billing server bills the insurance company for reimbursement. At step 820, the control server 705 recognizes and tracks the use of the vial and, if the number of vials goes below a par level, communicates with the billing server 715 to order more product. At step 825, billing server 715 requests a refill from manufacturer 610 by placing an order with the manufacturer 610 for more product.

The manufacturer 610 then ships product; generates a tracking number, manifest, and invoice; and sends the information to the billing server 715 at step 830. The billing server 715 relays the tracking number and manifest to the control server 705 and to the product partner 640 at step 835. The vending refrigerator 100 is then refilled at step 840, and it notifies the control server 705 when it has been refilled at step 845. Then, at step 850, the control server 705 informs billing server 715 of product delivery and updated inventory levels. The billing server 715 then settles the manufacturer's invoice for the cost of the product at 855. The process is completed when the billing server 715 receives reimbursement from insurance at step 860.

An exemplary general system flow for the above-described system is as follows. It is contemplated that fill orders can be submitted through the vending refrigerator 100 key pad, a smart phone, or a mobile device with a software application that receives information from the vending refrigerator and that can be communicatively connected with the system, e.g., the control server 705 or billing server 715. The filling system may also be controlled through a web page communicatively connected with the vending refrigerator 100, e.g., through the control server 705 or the billing server 715.

The vending refrigerator 100 may capture product information through the use of a bar code scanner. The bar code scanner may be located on the control compartment. The person that is charged with filling the vending refrigerator 100 can scan each product, e.g., a vaccine, before re-filling the product dispenser 190. The vending refrigerator may contain a server on its control compartment 115 that maintains communication between the user's office and a control server 705 at a vendor that manufactures and maintains the vending refrigerator 100. The vending refrigerator 100 may report every movement of product and event or alarm requiring action to the vending refrigerator 100 manufacturer.

As explained above, the product dispensers 190 and 191 do not allow a product to be returned through the dispenser drawer 360 or 420. If a product is removed, it can be placed on a dispensing shelf, e.g., 181 that does not contain any product dispensers 190, 191 and that does not have any sensors. Optionally, products that allow for multiple dosages can be placed in the dispensing shelf, e.g., 181, that does not have any sensors or product dispensers 190, 191 after initial dosing from such product. Preferably, vending refrigerator 100 only tracks whether a product is in a product dispenser 190, 191. The user is responsible for tracking payments and distribution of the product in such multiple dosage cases.

A doctor and/or nurse may utilize the following exemplary process in using the vending refrigerator 100. The doctor, nurse, or other user logs-in using his or her own unique user code. The user opens the door of vending refrigerator 100 and pulls the required vial from the drawer of the product dispenser 190, 191. If the user pulls the wrong vial, the vial is placed on the dispensing shelf, e.g., 181, that does not have any sensors or product dispensers 190, 191. Similarly, if the product is a multi-dose vaccine, the remainder will be placed on the dispensing shelf, e.g., 181, that does not have any sensors or product dispensers 190, 191. The user then closes the door 105 of vending refrigerator 100, provides the product to the patient or ultimate recipient, records the dosing in POMIS, and disposes of the vial or syringe under normal operation procedures. Dispensing is registered in vending refrigerator 100 and relayed to the manufacturer of the vending refrigerator 100 or any other party monitoring the refrigerator's use. The billing system is preferably configured to ensure the product, e.g., vaccine, is billed within 24 hours of use to the insurance company. Refill orders are preferably placed when stock levels are reduced or at specific intervals.

In a further exemplary process employed by a product specialist, the vending refrigerator 100 may be optimally used in accordance with the following process. The vending refrigerator 100 manufacturer or manager establishes an initial inventory or product, e.g., vaccines. When a product vial is removed from the vending refrigerator 100, the reduction of inventory is recorded in the control compartment 110 and relayed to the managing partner 605 or control server 705. The managing partner 605 or control server 705 recognizes when a stock level, and more preferably an unexpired stock level, falls below par and notifies the billing server 715 or partner designated to place and manage product orders. The billing server 715, or the partner designated to manage orders, places an order with the product manufacturer 610. The product manufacturer 610 ships the order to and alerts the billing server 715 of the tracking information, which is then relayed to the control server or manufacturer/manager of the vending refrigerator 100.

The billing server 715 or party designated to manage orders notifies a product partner and the manufacturer/manager of the data received from the vending refrigerator 100, including preferably that there are X deliveries of specific products occurring the following day for scheduling purposes. The product partner schedules a time to visit the user's office and replenishes the vending refrigerator 100 from the delivered product order. If the delivery arrives prior to the arrival of the product partner specialist, the user may place the product in an appropriate refrigerator to maintain temperature control.

The product partner specialist verifies the thermal indicator on the box is in proper condition; logs in via the keypad using a unique code; unlocks the vaccine compartment; replaces the product in accordance with industry standards (e.g., using First-In, First-Out (FIFO) principle); and scans the bar code of each vial and interacts with the vending refrigerator 100 front panel LCD/touchscreen to identify the product to be loaded. The vending refrigerator 100 and the manager of the vending refrigerator 100 or manufacturer's software preferably records the product name, the number of doses received, the date the product was received, the condition of the product on arrival, the product manufacturer, the lot number and product expiration date, as determined by the scanner and the front panel dialog. The vending refrigerator may include a flashing LED(s) under the cartridge/slot to indicate which one to fill, and the refiller preferably verifies that the vaccine being replaced is going into the correct cartridge/slot one at a time. Expired products are preferably removed and sent to the manufacturer for reimbursement and/or replacement. Expired vaccines may occur due to power outages, being past their expiration date, or temperature fluctuations.

It is contemplated that the control server 705 may be configured to allow for the return of expired products. This option could be included under an inventory menu option entitled "return to manufacturer/expired product." Expired products in the product dispensers 190, 191, or on the dispensing shelf, e.g., 181, which does not have any sensors or product dispensers 190, 191, can also be returned to the product manufacturer for disposal and/or reimbursement.

The product partner specialist ensures that all unexpired (and unrecalled) vials on the dispensing shelf, e.g., 181, which does not have any sensors or product dispensers 190, 191, will remain there for future use. He or she then locks the vaccine compartment, replaces any miscellaneous items as needed (labels, boxes, containers, etc.), and checks in with the user to see if there are any issues of any sort.

The product specialist also asks whether there are any maintenance items needing to be checked, and informs the manufacturer and/or manager of the vending refrigerator 100. The temperature of the vending refrigerator 100 is automatically controlled, such that there would be no need for the product specialist to record such information. The product specialist then provides a summary of product usage, preferably for the month, and answers any product related questions.

In accordance with an aspect of an embodiment of the invention, the system employs an exemplary inventory reconciliation process as follows. The product specialist may conduct a physical inventory of the vending refrigerator 100 for reconciliation with the automated vending refrigerator 100 and manufacturer/control server 705 recorded inventory levels. The product specialist or other user conducting the inventory interacts with the vending refrigerator 100 LCD/touchscreen 130 dialog or user input device 140 to note any and all inventory discrepancies. The recorded vending refrigerator 100 and manufacturer/control server 705 inventory levels are adjusted to match the physical inventory, with a time stamped note explaining the adjustment.

In some instances, it may become desirable to modify the input menus. An exemplary menu change process may include the following steps. If product demand is expected to change, e.g., required for back-to-school or flu season when certain vaccines will be in higher demand, then the menu and inventory may be changed. The product partner may evaluate the need for a second vending refrigerator 100 or to change the quantity of product supplied. The product partner may submit a "menu change" to the manufacturer or manager of vending refrigerator 100. The manager or manufacturer will then build the new menu and download the new menu to the vending refrigerator through the network. The manufacturer or manager of vending refrigerator 100 may store all historical data on a server to be used for analysis as needed, such as location, product type (e.g., vaccine), and user. The product specialist arrives to the user's office and contacts the manager or manufacturer technical department for assistance with completing the menu change. The system is designed to include procedures when there is product remaining in the affected cartridge(s)/slot(s). For example, an "Extraction" option allows for movement of product without generating a billing invoice or replenishment order. The inventory is reloaded and the system is updated.

If there is a malfunction or an alarm is otherwise activated, the system is configured to employ the following process. Once an alarm is activated, the vending refrigerator 100 records the alarm and relays notification of the alarm to the manufacturer/manager of the vending refrigerator 100. The service telephone number is preferably displayed on the vending refrigerator display. The manufacturer/manager may notify the product specialist as soon as possible via e-mail, SMS, or any other electronic means. The product specialist preferably contacts the user to determine the cause of the alarm (e.g., unplugged unit, temperature drop, etc.) and to resolve the problem (if able). The product specialist may follow a specified protocol. The result of the call is logged on the manufacturer/manager database for evaluation by management. The information collected may include the date, name of the person spoken to, time, and any other pieces of information deemed to be crucial by the user, manufacturer or service provider. The product specialist may contact the manufacturer/manager of the vending refrigerator 100 for technical support if the issue remains unresolved. The manufacturer/manager may then send a technician as needed. Items that the technician may check include the length of back-up power available from the battery—48 hour minimum, 72 hour preferred, which allows for holiday weekends when the office may be closed for three days.

The following events are examples of items that might cause an alarm to be triggered: out of temperature range, door open beyond a predetermined period of time, no main power (i.e., switched over to battery), impending total power loss (i.e., no main and battery drained), no communication to server, illegal access or access try count exceeded, specific cartridge/slot not communicating, low batteries (test AC/DC load), dispensing an expired vaccine, and dispensing a recalled or quarantined vaccine. Records may be stored, such as for three years on the manufacturer's server, or as required by applicable law or business practice.

In an embodiment, the vending refrigerator 100 may provide redundant systems to address possible power outages. The vending refrigerator 100 may include a back-up battery to provide power in the event of a power failure. The vending refrigerator 100 may be programmed to lock and to not dispense product in order to maintain temperature and protect the stored products. A lock override upon entry of a special access code may be provided to allow emergency entry or for removal of product to another location. In addition, after a configurable time interval, the chilled or freezer compartments may be shut down to conserve battery power and the lock will continue to remain locked during this stage. Once the battery fails completely, the vending refrigerator 100 will be left in an unlocked state.

A process may also be implemented to address recall and quarantine of stored products. In such event, the manufacturer/manager will record the recall/quarantine for a specific product, e.g., vaccine, including lot number on the vending refrigerator 100. The product will be identified to be "On Hold" on the vending refrigerator 100 display. In some embodiments, the product dispenser 190, 191 will be locked to prevent dispensation of the product. The vending refrigerator 100 may also flash LED(s) to warn against use of a product, display a warning on the front panel display, raise an alarm if quarantined product is dispensed, and lock down under software-configurable conditions. A product specialist may remove recalled vaccine from vending refrigerator 100 after entering a code and place such recalled vaccine in the user's refrigerator until resolved or remove it to its own facility.

The system can be further configured to allow transfer of vaccines between different locations, e.g., between physician offices in a vaccine partner territory. Software to implement the system may implement the following process. First, the manufacturer sets inventory levels for management of the process. The vending refrigerator 100 and the manufacturer software has the ability to accept transfer vaccine from another user. The software may include transport practices established for a vaccine specialist, e.g., ability of a transport receptacle with 12-volt DC power convertor to cool the container as an option that can be plugged into electrical receptacles in a vehicle. The software also tracks temperature for cold chain. In some instances, the transport receptacle may be another vending refrigerator 100 into which a magazine or module can be plugged, and that is powered by a car. This special software would be used for transport only.

The software and system may also include solutions for discrepancies and errors. In one exemplary embodiment, when shipping errors occur, the product specialist matches the billing server or partner shipping request to the product manufacturer shipping document and alerts that billing server or partner of discrepancies. The software may include a validation process to cross check that what was ordered is what was delivered and subsequently placed in the individual cartridge/slot at the product dispenser 190, 191.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

What is claimed is:

1. A vending refrigerator, comprising:
   a control compartment comprising a processor having computer executable code configured to receive and store inventory data from said vending refrigerator;
   a first dispensing shelf in data communication with said control compartment;
   a first removable product dispenser on said first dispensing shelf comprising a first storage compartment storing a plurality of containers of a first product and a first dispensing drawer horizontally extensible from a bottom of said first storage compartment and configured to sequentially dispense a single one of said containers of said first product upon each horizontal extension of said first dispensing drawer from said first storage compartment, wherein said first product dispenser is configured to sequentially position one of said first product containers in said first dispensing drawer upon closure of said first dispensing drawer, and wherein said first product dispenser further comprises a movable guard movable to a position that prevents replacement of the first product back into the product dispenser through the first dispensing drawer when said first dispensing drawer is open, and prevents closure of the first dispensing drawer until removal of said first product from said first dispensing drawer;
   a second dispensing shelf in data communication with the control compartment; and
   a second removable product dispenser on said second dispensing shelf comprising a second storage compartment storing a plurality of containers of a second product and a second dispensing drawer horizontally extensible from a bottom of said second storage compartment and configured to sequentially dispense a single one of said containers of said second product upon each horizontal extension of said second dispensing drawer from said second storage compartment, wherein said second product dispenser is configured to sequentially position one of said second product containers in said second dispensing drawer upon closure of said second dispensing drawer, and wherein said second product dispenser prevents replacement of the second product back into the product dispenser through the dispensing drawer when said second dispensing drawer is open.

2. The vending refrigerator of claim 1, further comprising a chilled compartment and a freezer compartment.

3. The vending refrigerator of claim 2, wherein the chilled compartment and the freezer compartment each comprises the first dispensing shelf, the first product dispenser, the second dispensing shelf, and the second product dispenser.

4. The vending refrigerator of claim 1, further comprising a first product detection sensor element on said first dispensing shelf, and a second, movable product detection sensor element movable within said first product dispenser, wherein said second product detection sensor element is movable in response to a first product being positioned for loading into said first dispensing drawer, and wherein movement of said first sensor element with respect to said second sensor element generates a signal to said processor indicating the presence of a product ready for loading into the first dispensing drawer.

5. The vending refrigerator of claim 4, further comprising a first drawer position sensor element on said first dispensing shelf, and a second drawer position sensor element attached to and movable with said first dispensing drawer, wherein movement of said first drawer position sensor element with respect to said second drawer position sensor element generates a signal to said processor indicating a position of the first dispensing drawer.

6. The vending refrigerator of claim 1, further comprising a third dispensing shelf, wherein the third dispensing shelf is configured to store said first product or second product after said first product or said second product is dispensed from the first product dispenser or the second product dispenser.

7. The vending refrigerator of claim 4, wherein said first product detection sensor element is in data communication with said processor.

8. The vending refrigerator of claim 7, said processor further comprising computer executable code configured to record dispensing of product from said first product dispenser.

9. The vending refrigerator of claim 1, further comprising a first door covering a portion of said first product dispenser and positioned to block removal of said first product dispenser from said vending refrigerator, and a second door covering a portion of said second product dispenser and positioned to block removal of said second product dispenser from said vending refrigerator.

10. The vending refrigerator of claim 9, wherein said first door is positioned so as to not extend over said first dispensing drawer, and wherein said second door is positioned so as to not extend over said second dispensing drawer.

11. The vending refrigerator of claim 9, wherein said first door further comprises a first electronic lock, and wherein said second door further comprises a second electronic lock.

12. The vending refrigerator of claim 11, wherein said first electronic lock and said second electronic lock are in data communication with said processor, said processor further comprising computer executable code configured to unlock at least one of said first electronic lock and said second electronic lock.

13. A system for dispensing products, comprising:
a vending refrigerator in data communication with a computer network, said vending refrigerator comprising:
   a control compartment comprising a processor having computer executable code configured to receive and store inventory data from said vending refrigerator;
   a first dispensing shelf in data communication with said control compartment;
   a first removable product dispenser on said first dispensing shelf comprising a first storage compartment storing a plurality of containers of a first product and a first dispensing drawer horizontally extensible from a bottom of said first storage compartment and configured to sequentially dispense a single one of said containers of said first product upon each horizontal extension of said first dispensing drawer from said first storage compartment, wherein said first product dispenser is configured to sequentially position one of said first product containers in said first dispensing drawer upon closure of said first dispensing drawer, and wherein said first product dispenser further comprises a movable guard movable to a position that prevents replacement of the first product back into the product dispenser through the first dispensing drawer when said dispensing drawer is open, and prevents closure of the first dispensing drawer until removal of said first product from said first dispensing drawer;
   a second dispensing shelf in data communication with the control compartment; and
   a second removable product dispenser on said second dispensing shelf comprising a second storage compartment storing a plurality of containers of a second product and a second dispensing drawer configured to sequentially dispense a single one of said containers of said second product, wherein said second product dispenser is configured to sequentially position one of said second product containers in said second dispensing drawer upon closure of said second dispensing drawer, and wherein said second product dispenser prevents replacement of the second product back into the product dispenser through the dispensing drawer; and
a control server in data communication with said vending refrigerator through said data network;
said processor further comprising computer executable code configured to send said inventory data to said control server.

14. The system of claim 13, wherein said processor further comprises computer executable code configured to send data to said control server indicative of historical temperatures inside of said vending refrigerator.

15. The system of claim 14, wherein said processor further comprises computer executable code configured to send data to said control server indicative of predetermined alarm conditions having been reached in said vending refrigerator.

16. The system of claim 13, said vending refrigerator further comprising a first product detection sensor element on said first dispensing shelf, and a second, movable product detection sensor element movable within said first product dispenser, wherein said second product detection sensor element is movable in response to a first product being positioned for loading into said first dispensing drawer, and wherein movement of said first sensor element with respect to said second sensor element generates a signal to said processor indicating the presence of a product ready for loading into the first dispensing drawer.

17. The system of claim 16, said vending refrigerator further comprising a first drawer position sensor element on said first dispensing shelf, and a second drawer position sensor element attached to and movable with said first dispensing drawer, wherein movement of said first drawer position sensor element with respect to said second drawer position sensor element generates a signal to said processor indicating a position of the first dispensing drawer.

18. The system of claim 16, wherein said first product detection sensor element is in data communication with said processor.

19. The system of claim 18, said processor further comprising computer executable code configured to record dispensing of product from said first product dispenser.

20. The system of claim 13, said vending refrigerator further comprising a first door covering a portion of said first product dispenser and positioned to block removal of said first product dispenser from said vending refrigerator, and a second door covering a portion of said second product dispenser and positioned to block removal of said second product dispenser from said vending refrigerator.

21. The system of claim 20, wherein said first door is positioned so as to not extend over said first dispensing drawer, and wherein said second door is positioned so as to not extend over said second dispensing drawer.

22. The system of claim 20, wherein said first door further comprises a first electronic lock, and wherein said second door further comprises a second electronic lock.

23. The system of claim 22, wherein said first electronic lock and said second electronic lock are in data communication with said processor, said processor further comprising computer executable code configured to unlock at least one of said first electronic lock and said second electronic lock.

* * * * *